US007074570B2

(12) United States Patent
Palmgren et al.

(10) Patent No.: US 7,074,570 B2
(45) Date of Patent: Jul. 11, 2006

(54) PEPTIDE FRAGMENTATION

(75) Inventors: Ronnie Palmgren, Stockholm (SE); Jean-Luc Maloisel, Enebyberg (SE); Maria Liminga, Uppsala (SE); Thomas Woods Keough, Cincinnati, OH (US); Robert Scott Youngquist, Mason, OH (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 749 days.

(21) Appl. No.: 09/863,786

(22) Filed: May 23, 2001

(65) Prior Publication Data

US 2003/0032056 A1    Feb. 13, 2003

(51) Int. Cl.
G01N 33/53    (2006.01)
(52) U.S. Cl. ............... 435/7.1; 435/69.7; 436/119; 558/44
(58) Field of Classification Search ............. 435/7.1, 435/69.7; 436/173, 119; 558/44
See application file for complete search history.

(56) References Cited

U.S. PATENT DOCUMENTS

| 3,478,013 A | 11/1969 | Jones et al. | |
|---|---|---|---|
| 4,296,109 A | 10/1981 | Laurent et al. | |
| 5,470,753 A * | 11/1995 | Sepetov et al. | 436/89 |
| 5,821,063 A | 10/1998 | Patterson et al. | |
| 5,834,195 A * | 11/1998 | Benkovic et al. | 435/6 |
| 6,322,970 B1 * | 11/2001 | Little et al. | 435/6 |

FOREIGN PATENT DOCUMENTS

WO    WO 00/43792    7/2000

OTHER PUBLICATIONS

Maggio et al (Enzyme-Immunoassay, Department of Pathology, Scripps Clinic and Research Foundation, May 14, 1987).*

T. Keough, et al. "A method for high-sensitivity peptide sequencing using postsource decay matrix-assisted laser desorption ionization mass spectrometry" Proceedings of the National Academy of Sciences of USA, National Academy of Science, Washington, US vol. 96, Jun. 1999 pp. 7131-7136.

G. Fink, et al. "Reagents Suitable for the Cross Linking of Nucleic-Acids to Proteins" Analytical Biochemistry vol. 108, No. 2, 1980 pp. 394-401.

(Continued)

Primary Examiner—Long V. Le
Assistant Examiner—Deborah A. Davis
(74) Attorney, Agent, or Firm—Yonggang Ji

(57) ABSTRACT

The present invention relates to a method of identifying a polypeptide using a class of novel, water-stable reagents. More specifically, the method according to the invention comprises the steps of
(a) derivatization in an aqueous solution of the N-terminus of the polypeptide, or the N-termini of one or more peptides of the polypeptide, with at least one acidic reagent which comprises a sulfonyl moiety coupled to an activated acid moiety to provide one or more peptide derivatives;
(b) analyzing at least one such derivative using a mass spectrometric technique to provide a fragmentation pattern; and
(c) interpreting the fragmentation pattern.

Furthermore, the present invention also relates to a kit for identifying a polypeptide by a mass spectrometric technique, which kit comprises at least one acidic reagent comprising a sulfonyl moiety coupled to an activated acid moiety in a container together with suitable means for analysis of the fragmentation pattern obtained.

11 Claims, 19 Drawing Sheets

OTHER PUBLICATIONS

J. Keana, et al. "Detergents Containing a 1 3 Diene Group in the Hydrophobic Segment Facile Chemical Modification by a Diels Alder Reaction with Hydrophilic Dienophiles in Aqueous Solution" Journal of Organic Chemistry vol. 48, No. 16, 1983 pp. 2661-2666.

Spengler, B., et al. "Peptide Sequencing of Charged Derivatives by Postsource Decay MALDI Mass Spectrometry" International Journal of Mass Spectrometry and Ion Processes 169/170 (1997) pp. 127-140.

Keough, T., et al. "A Method for High-Sensitivity Peptide Sequencing Using Postsource Decay Matrix-Assisted Laser Desorption Ionization Mass Spectrometry" Proc. Natl. Acad. Sci. USA vol. 96, Jun. 1999, pp. 7131-7136.

Keough, T., et al. "Tandem Mass Spectrometry Methods for Definitive Protein Identification in Proteomics Research" Electrophoresis, 2000, vol. 21, pp. 2252-2265.

Keough, T., et al. "Derivatization Procedures to Facilitate *De Novo* Sequencing of Lysine-Terminated Tryptic Peptides Using Postsource Decay Matrix-Assisted Laser Desorption/ Ionization Mass Spectrometry" Rapid Communications in Mass Spectrometry, vol. 14, 2000, pp. 2348-2356.

Lacey, M. P., et al. "Improved Derivatization Chemistry Enabling *De Novo* Sequencing of Lysine-Terminated Tryptic Peptides Using Postsource Decay of MALDI MS" Poster, The Procter and Gamble Company.

* cited by examiner

US 7,074,570 B2

PEPTIDE FRAGMENTATION

TECHNICAL FIELD

The present invention relates to a method of identifying a polypeptide, wherein a novel class of reagents is used to derivatize peptides before analysis thereof using mass spectrometry. The invention also relates to a kit, which comprises such novel reagent(s) according to the invention as well as to novel reagents as such.

BACKGROUND

The identification and sequencing of polypeptides has become of increased importance with the rapid development of the field of proteomics, wherein the expression products of novel genes are examined as to their function and composition.

Matrix-assisted laser desorption ionization (MALDI) mass spectrometry is a method developed for peptide and polypeptide sequencing. (For a reference to the principles of MALDI mass spectrometry, see e.g. Spengler et al., "Peptide Sequencing by Matrix-assisted Laser-desorption Mass Spectrometry", Rapid Communications in Mass Spectrometry, Vol. 6, pp. 105–108 (1992).) MALDI mass spectrometry offers several advantages in the field of mass spectrometry. For example, it provides a higher sensitivity than the conventional electrospray triple quadropole equipment. When used in combination with time-of-flight (TOF) mass analyzers, MALDI mass spectrometry is also applicable to higher mass peptides than can be analyzed with triple quadropole equipment. MALDI mass spectrometry is also useful for analyzing complex mixtures with minimal sample purification. Electrospray ionization, on the other hand, is readily interfaced to powerful separation techniques including liquid chromatography (LC) and various forms of capillary electrophoresis (CE). Highly automated analyses are possible when using LC and CE as the sample purification and introduction devices.

However, current MALDI and, to a lesser extent, electrospray ionization mass spectro-metric methods fail to adequately offer predictable tandem mass spectrometry fragmentation patterns. For example, multiple ion series (including a-ions, b-ions, and y-ions) are often observed, resulting in MALDI post-source decay spectra that are too complex for efficient interpretation and sequencing. Multiple ion series (b- and y-ions), plus internal fragments and both singly and multiply charged ions are formed from multiply charged precursor ions generated by electrospray ionization, and the resulting tandem mass spectra are often difficult to interpret de novo. Accordingly, problems with fragmentation have limited the ability to rapidly sequence polypeptides using mass spectrometry. As a result, mass spectrometry, and particularly MALDI mass spectrometry, has been of limited value in this area.

Several research groups have attempted to improve the utility of mass spectrometry in the field of polypeptide sequencing through the use of chemical derivatization techniques. Such techniques have been utilised to promote and direct fragmentation in the MSMS spectra of peptides with the goal of increasing sensitivity and decreasing the complexity of the resulting spectra. Most of these methods provide cationic derivatives. For example, derivatization with a quaternary ammonium group, and analysis using the static SIMS ionization method has been suggested. However, application of such techniques using MALDI mass spectrometry and electrospray ionization with low-energy collisional activation have not proven generally effective.

More recently, for the determination of an amino acid sequence, Keough et al (WO 00/43792, in the name of The Procter & Gamble Company) have suggested a derivatization of the N-terminus of a polypeptide with one or more acidic moieties having pKa values of less than 2 before analysis by mass spectrometry of the analyte, such as with MALDI mass spectrometry. The acidic moiety is preferably a sulfonic acid or a disulfonic acid derivative. The derivatives promote a charge-site initiated cleavage of backbone amide bonds and they enable the selective detection of only a single series of fragment ions comprising the y-ions. However, the reaction according to Keough et al are generally performed under non-aqueous conditions due to the poor water stability of the reagents utilized therein. Accordingly, for a commercially useful determination of amino acid sequences by mass spectrometry, there is still a need for improved methods that fulfill the requirements especially for automated procedures.

SUMMARY OF THE INVENTION

One object of the present invention is to provide reagents for use in methods wherein a peptide or polypeptide is identified using a mass spectrometric technique, which reagents are more environmentally acceptable than the prior art use of organic solvents. This is achieved by using a novel class of water-stable derivatization reagents, which comprise a sulfonyl moiety coupled to an activated acid moiety, to provide peptide derivatives for analysis in a subsequent mass spectrometry step. A further object of the invention is to provide a simplified and hence easily automated procedure for derivatizing peptides or polypeptides prior to identification with mass spectrometric techniques. This is achieved by providing a novel class of reagents, which reagents exhibit an improved aqueous stability as compared to the prior art reagents.

Thus, the present invention relates to a method of identifying a polypeptide, which method comprises the steps of:
(a) derivatization in an aqueous solution the N-terminus of the polypeptide, or the N-termini of one or more peptides of the polypeptide, with at least one acidic reagent comprising a sulfonyl moiety coupled to an activated acid moiety to provide one or more peptide derivatives, which reagent exhibits a half-life in aqueous solution of not less than 10 minutes, preferably not less than about 20 minutes and most preferably not less than about 30 minutes at room temperature;
(b) analyzing at least one such derivative using a mass spectrometric technique to provide a fragmentation pattern; and
(c) interpreting the fragmentation pattern obtained.

The objects of the invention are more specifically achieved as defined by the appended claims. Below, the present invention will be described in more detail with reference to specific embodiments and illustrative examples thereof.

BRIEF DESCRIPTION OF THE DRAWINGS

FIG. 2A shows the stability of 3-sulfopropionic acid NHS-ester in $D_2O$ while FIG. 2B shows the stability of 2-sulfobenzoic acid NHS-ester in $D_2O$.

DEFINITIONS

Figure 1A:
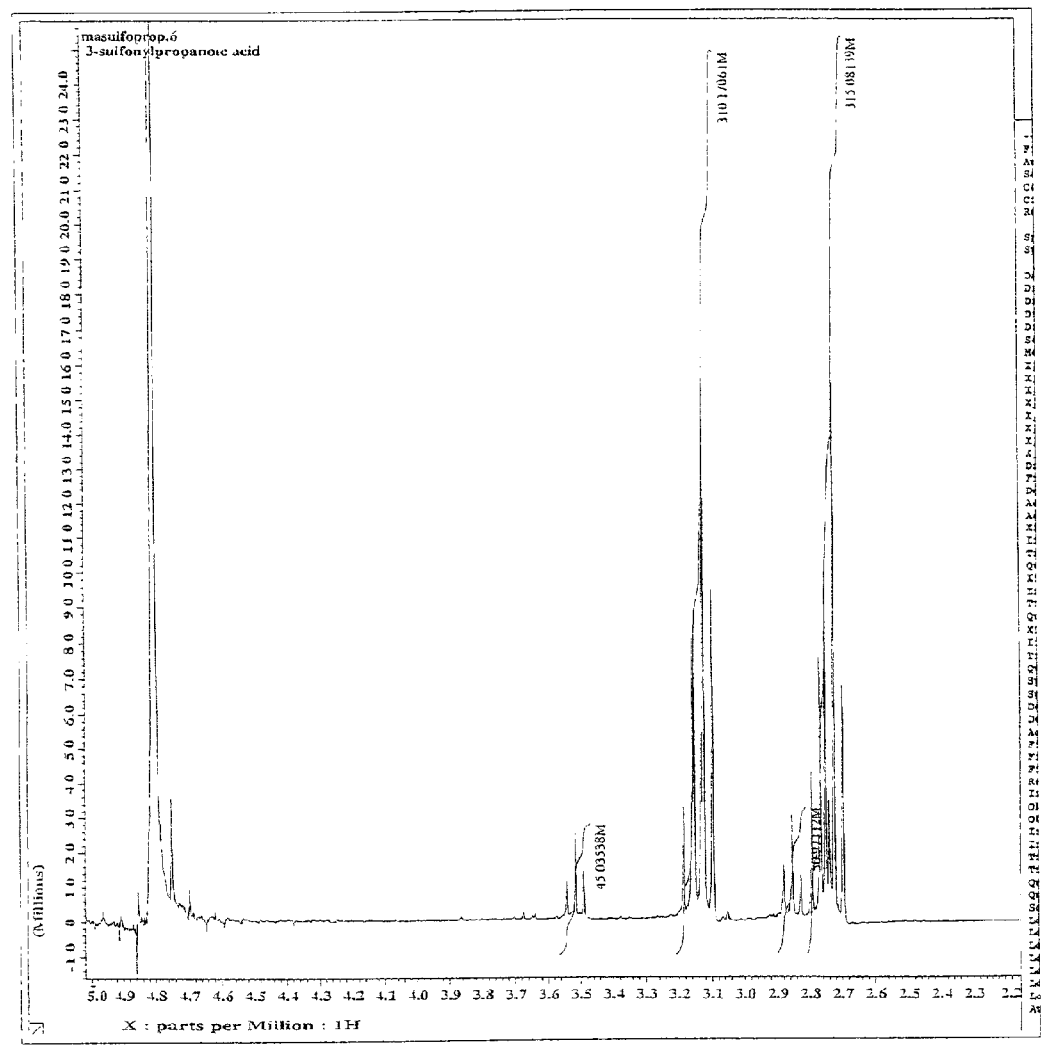
FIG. 1A–D show NMR-spectra as discussed in example 1 below.

In the present specification, the term "identifying" is not necessarily synonymous with determining the complete sequence, since it also includes partial sequence determination for identifying the polypeptide or characterizing it as similar to or different from a peptide derived from a known protein. Further, it also includes making a tentative identification based on the most probable of a small number of possibilities.

Further, the term "ionization" as used herein refers to the process of creating or retaining on an analyte an electrical charge equal to plus or minus one or more electron units.

The term "aqueous environment" as used herein includes any water-based solution, suspension or any other form, which contains less about 10% of organic solvents.

As used herein, the term "electrospray ionization" refers to the process of producing ions from solution by electrostatically spraying the solution from a capillary electrode at high voltage with respect to a grounded counter electrode. The definition is intended to include both electrospray ionization and pneumatically assisted electrospray ionization, which is also referred to as ionspray. As used herein, the term "electrospray ionization" applies to all liquid flow rates and is intended to include microspray and nanospray experiments. Moreover, the definition is intended to apply to the analyses of peptides directly infused into the ion source without separation, and to the analysis of peptides or peptide mixtures that are separated prior to electrospray ionization. Suitable on-line separation methods include, but are not limited to, HPLC, capillary HPLC and capillary electrophoresis. Electrospray ionization experiments can be carried out with a variety of mass analyzers, including but not limited to, triple quadrupoles, ion traps, orthogonal-acceleration time-of-flight analyzers and Fourier Transform Ion Cyclotron Resonance instruments.

As used herein, the term "polypeptide" refers to a molecule having two or more amino acid residues.

As used herein, the term "wild-type" refers to a polypeptide produced by unmutated organisms.

As used herein, the term "variant" refers to a polypeptide having an amino acid sequence which differs from that of the wild-type polypeptide.

The term "water stable" as used herein refers reagents having a half-life in aqueous solution of not less than 10 minutes, preferably not less than about 20 minutes and most preferably not less than about 30 minutes at room temperature.

The term "activated acid" refers to an acid derivative, preferably a carboxylic acid derivative, which is capable of forming amide bonds in a aqueous environment.

As used herein, the following abbreviations are used:

| | |
|---|---|
| Tetrahydrofuran | THF |
| N-hydroxysuccinamide | NHS |
| Dichloromethane | DCM |
| N,N-diisopropylethylamine | DIEA |
| Trifluoroacetic acid | TFA |
| Deuterated water | $D_2O$ |
| Hydrochloric acid | HCl |
| Thionyl chloride | $SO_2Cl$ |
| Ethyl acetate | EtAc |
| Methanol | MeOH |
| Room Temperature and Pressure | RTP |
| Room Temperature | RT |
| Milli-Q purified water | MQ |
| O-(N-Succinimidyl)-N,N,N',N'-tetramethyluronium $BF_4$ | TSTU |
| Acetonitrile | ACN |
| Trifluoroacetic acid | TFA |
| Deuterated chloroform | $CDCl_3$ |
| Thin layer chromatography | TLC |

DETAILED DESCRIPTION OF THE INVENTION

A first aspect of the present invention is a method of identifying a polypeptide, which method comprises the steps of (a) derivatization in an aqueous solution of the N-terminus of the polypeptide, or the N-termini of one or more peptides of the polypeptide, with a least one acidic reagent comprising a sulfonyl moiety coupled to an activated acid moiety to provide one or more peptide derivatives, which reagent exhibits a half-life in aqueous solution of not less than 10 minutes, preferably not less than about 20 minutes and most preferably not less than about 30 minutes at RT;

(b) analyzing at least one such derivative using a mass spectrometric technique to provide a fragmentation pattern; and (c) interpreting the fragmentation pattern obtained.

The present method is useful for sequencing polypeptides, such as wild-type, variant and/or synthetic polypeptides. The method is especially useful for identifying high molecular weight polypeptides for use e.g. in the biological and pharmaceutical field. More specifically, the present method can be used to facilitate biological studies requiring rapid determination of peptide or polypeptide sequences; to identify post-translational modifications in proteins and to identify amino acid modifications in variant proteins, such as those used in commercial laundry and cleansing products; to aid in the design of oligonucleotide probes for gene cloning; to rapidly characterize products formed in directed evolution studies; in combinatorial and peptide library identification; and in proteomics.

Thus, in step (b), the present invention utilizes a mass spectrometric technique for the analysis of the derivative(s), which technique can include matrix-assisted laser desorption ionization (MALDI) mass spectrometry or electrospry ionization. These ionization techniques can can be carried out with a variety of mass analyzers, including but not limited to, triple quadrupoles, ion traps, orthogonal-acceleration time-of-flight analyzers and Fourier Transform Ion Cyclotron Resonance instruments. The spectra obtained are routinely interpreted de novo in accordance with standard procedure. However, in the most preferred embodiment, in step (b), MALDI mass spectrometry is used. MALDI mass spectrometers are commercially available and described in the literature, see e.g. Kussmann M. and Roepstorff P., Spectroscopy 1998, 14:1–27.

Thus, even though sulfonic groups have been added to the N-termini of peptides to facilitate sequencing with MALDI mass spectrometry in the prior art, the previously used reagents have been limited to those exhibiting a low stability in water. (In this context, see e.g. T. Keough, R. S. Youngquist and M. P. Lacey, *Proc.Natl. Acad. Sci. USA.*, 96, 7131 (1999); T. Keough, M. P. Lacey, A. M. Fieno, R. A. Grant, Y. Sun, M. D. Bauer and K. B. Begley, *Electrophoresis*, 66 2252 (1999); and T. Keough, M. P. Lacey and R. S. Youngquist, *Rapid Commun. Mass Spectrom.* 14, 2348 (2000).)

The present invention provides for the first time a one-step method wherein a water-stable reagent is used for the derivatization step preceding the actual mass spectrometry analyses. The advantages of working with a water-soluble reagent and avoiding organic solvents are obvious and include easier automation of the derivatization procedure because no dry down steps and solvent changes are required.

In addition, the present inventors have surprisingly shown that with one or more of the novel water-stable reagents, it is possible to obtain a peptide derivatization efficiency, which is superior to that of the prior art methods. The novel derivatives are also more stable in water than the prior art reagents. Thus, the present invention provides a method which is more robust than any previously suggested technology.

An essential advantage of the present method when compared to the previously suggested technology (see e.g. the above mentioned WO 00/43792, Keough et al) resides in the fact that according to the present invention, all steps can be carried out under aqueous conditions. As the previously suggested technology required two dry down steps and several pH changes from basic to acidic, and vice versa, the present method is much more amenable to automation. To illustrate the above, the known method to derivatize peptide extracts from in-gel digests can be summarized as follows:
1. Peptide extract in 240 µL solution (50% acetonitrile).
2. Concentrate to about 25 µL on a speed vac.
3. Add DIEA, guanidinate lysine side-chains overnight at RT (basic).
4. Add HCl, cleanup on a $C_{18}$ µZipTip™ (acidic).
5. Dry completely to remove water.
6. Reconstitute in 10 µL THF:DIEA 19:1 (basic).
7. Add 2 µL reagent (2 µL neat chlorosulfonylacetyl chloride in 1 mL THF).
8. React 1 to 2 min. at RT.
9. Dry completely to remove organics and excess base.
10. Reconstitute in 10 µL of 0.1% TFA (acidic).

However, the method according to the invention will only require 4 steps, summarized as follows:
1. Concentrate peptides from in-gel digest to about 20 µL.
2. Add DIEA, guanidinate lysine side-chains overnight at RT.
3. Add water-compatible sulfonation agent, 30 minutes RT.
4. Add HCl, cleanup on a $C_{18}$ µZipTip™.

Thus, the present method is especially useful for the automated derivatization and/or partial characterization of proteins, e.g. in proteomics research.

Accordingly, in an especially advantageous embodiment, the present method is a computer assisted method, wherein suitable software is utilized in step (c). Thus, data analysis of mass-to-charge ratios obtained by the mass spectrometry is used for the interpretation of the fragmentation pattern obtained. Several software programs have been developed to compare mass spectra of the peptides obtained e.g. from MALDI-TOF experiments with theoretical spectra from proteins. The subject has for example been reviewed by Kussmann and Roepstorff (Kussmann M. and Roepstorff P., Spectroscopy 1998, 14:1–27).

A further advantage of the novel reagents according to the invention resides in the fact that they are easily stored in a crystalline form. Thus, the stability during storage and accordingly the shelf life of the reagents is greatly improved. Consequently, the present invention provides reagents which makes possible a less costly handling, and which also simplifies the practical use thereof in many routine procedures.

In a preferred embodiment, the present reagent has a pKa of less than about 2, preferably less than about 0 and most preferably less than about −2 when coupled with a peptide or polypeptide. The skilled person in this field can measure pKa values of acidic moieties as covalently coupled to a polypeptide or peptide using standard methods well known in the art. For example, such methods may include titration or an electrochemical method.

In one advantageous embodiment, the activated acid moiety of the reagent is an N-hydroxysuccinimide (NHS) ester.

In a specific embodiment of the present method, the acidic reagent comprising a sulfonyl moiety coupled to an NHS ester moiety is a 3-sulfopropionic acid N-hydroxysuccinimide ester.

In an alternative embodiment, the reagent is a 2-sulfobenzoic acid N-hydroxysuccinimide ester.

As the skilled in this field will realise, said reagent(s) can be used combined with any suitable buffer, as long as it is not reactive. Alternatively, they are simply used as dissolved in water. Furthermore, in the present method, it is to be understood that even though for practical reasons one single reagent is normally used, the invention also encompasses a method utilizing a mixture of two or more such reagents, each one of which being defined by comprising a sulfonyl moiety coupled to an NHS-ester moiety.

The preparation of the above mentioned exemplary reagents will be illustrated below in the experimental part of the present application. The activated acids of the present invention are prepared according to methods which are well-known to those ordinarily skilled in the art. The starting materials used in preparing the compounds of the invention are known, made by known methods, or are commercially available as a starting material.

It is recognized that the ordinarily skilled artisan in the art of organic chemistry can readily carry out standard manipulations of organic compounds without further direction. Examples of such manipulations are discussed in standard texts such as J. March, *Advanced Organic Chemistry*, John Wiley & Sons, 1992.

The ordinarily skilled artisan will readily appreciate that certain reactions are best carried out when other functionalities are masked or protected in the compound, thus increasing the yield of the reaction and/or avoiding any undesirable side reactions. Often, the ordinarily skilled artisan utilizes protecting groups to accomplish such increased yields or to avoid the undesired reactions. These reactions are found in the literature and are also well within the scope of the ordinarily skilled artisan. Examples of many such manipulations can be found in, for example, T. Greene, *Protecting Groups in Organic Synthesis*, John Wiley & Sons, 1981.

The compounds of the present invention may be prepared using a variety of procedures known to those ordinarily skilled in the art. Non-limiting general preparations include the following.

The activated acids of the invention can be prepared by activating the acid in a compound of the general structure below followed by reaction to generate a water stable reagent of the invention.

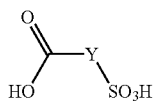

Where:
Y=a spacer which contains aliphatic and/or aromatic fragments and may optionally include additional sulfonic acids Non-limiting examples of appropriate acids are e.g. 2-sulfoacetic acid, 3-sulfopropionic acid, 3-sulfobenzoic acid 4-sulfobenzoic acid, 2-bromo-5-sulfobenzoic acid and 2-sulfobenzoic acid. For a general reference to sulfonyl groups useful to this end, see e.g. WO 00/43792.

Those skilled in the art will realize that in addition to the protonated acids of these compounds, the salts including, but not limited to sodium and potassium will be useful for the synthesis of compounds of the invention. Most of the activated acids can be easily prepared with common methods of the art (Recent reviews and books for peptide synthesis and preparation of activated esters: a) Alberico, F.; Carpino, L. A., Coupling reagents and activation., *Method. Enzymol.*, 1997, 289, 104–126. b) Bodansky, M.; Principles of Peptide Synthesis, 2$^{nd}$ ed., Springer-Verlag:Berlin, 1993. c) Humphrey, J. M., Chamberlin, A. R., Chemical Synthesis of Natural Product Peptides: Coupling Methods for the Incorporation of Noncoded Amino Acids into Peptides. *Chem. Rev.*, 1997, 97, 2243–2266. d) Handbook of Reagents for Organic Synthesis: Activating Agents and Protecting Groups, Pearson, A. J. and Roush, W. R., ed., John Wiley & Sons, 1999). Reactive derivatives of this structure include, for example, activated esters such as 1-hydroxybenzotriazole esters, mixed anhydrides of organic or inorganic acids such as hydrochloric acid and sulfonic acids, and symmetrical anhydrides of the acids of this structure. These activated materials may be directly useful as water-stable reagents of the invention: however; highly reactive materials such as acid chlorides may not be water stable as defined herein but can be further reacted with reagents such as N-hydroxysuccinamide to generate active acids that are water stable reagents of the invention.

Of the numerous reactive esters found in the literature, N-hydroxysuccinimide derived esters (Anderson, G .W.; Zimmerman, J. E.; Callahan, F. M.; *J. Am. Chem. Soc.*, 1964, 86, 1839, For a review see Klausner, Y. S.; Bodansky, M. S., Synthesis, 1972, 453), ortho and para-nitrophenyl esters (Bodansky, M.; Funk, K. W., Fink, M. L.; *J. Org. Chem.*, 1973, 38, 3565, Bodansky, M.; Du Vigneaud, V.; *J. Am. Chem. Soc.*, 1959, 81, 5688), 2,4,5-trichlorophenyl esters (Pless, J.; Boissonnas, R. A., *Helv. Chim. Acta;* 1963, 46, 1609), pentachlorophenyl (Kovacs, J.; Kisfaludy, L., Ceprini, M. Q., *J. Am. Chem. Soc.*, 1967, 89, 183) and pentafluorophenyl esters (Kisfaludy, L., Roberts, J. E., Johnson R. H., Mayers, G. L., Kovacs, J.; *J. Org. Chem.*, 1970, 35, 3563) are of the most practical interest. Other acid activating moieties include, thio esters such as 2-pyridylthio esters (Lloyd, K.; Young, G. T.; *J. Chem.Soc. (C)*, 1971, 2890), cyanomethyl esters (Schwyzer, R.; Iselin, B.; Feurer; M., *Helv. Chim. Acta;* 1955, 38, 69), N-acylimidazolides (Wieland, T.; Vogeler, K., *Angew.Chem.*, 1961, 73, 435), acyl azide (Curtius, T., *Ber.dtsch.Chem.Ges.*, 1902, 35, 3226 Fujii, N.; Yajima, H., *J. Chem. Soc. Perkin Trans I*, 1981, 789) or benzotriazol derived intermediate (Dormoy, J. R.; Castro, B., *Tetrahedron*, 1981, 37, 3699) are as well considered.

The use of these activated ester can as well be combined with selected acylation catalysts such as for example 4-dimethylaminopyridine (Hoefle, G.; Steglich, W.; Vorbrueggen, H., *Angew. Chem., Int. Ed. Engl.*, 1978, 17, 569. Scriven, E. F. V., *Chem. Soc. Rev.*, 1983,12, 129).

However, the exact molecular structure of the reagent is not essential, as long as said sulfonyl moiety and the activated acid moiety are present and provided that its water-stable nature and chemical reactivity with amines are retained. Accordingly, all such reagents which are water-stable and reactive are within the scope of the present invention. Further routine experimentation can subsequently be performed in order to identify e.g. an optimal pH for the reaction, or a specific activated acid, for which unwanted side reactions e.g. at hydroxyl groups are minimized.

The polypeptide, or peptides thereof, may be obtained by any means. For example, if necessary, the polypeptide of interest is isolated for analysis. Several procedures may be utilized for isolation including for example one-dimensional and two-dimensional electrophoresis. Alternatively, the polypeptides may have been synthesized through combinatorial chemistry methods well known in the art. In this instance, it is most preferable to synthesize a polypeptide having a basic or hydrophobic residue, preferably a basic (most preferably arginine or lysine), at or near the C-terminus of the resulting polypeptide.

Digestion may occur through any number of methods, including in-gel or on a membrane, preferably in-gel (see e.g. Shevchenko et al., "Mass Spectrometric Sequencing of Proteins from Silver-Stained Polyacrylamide Gels", Analytical Chemistry, Vol. 68, pp. 850–858 (1996)). Thus, in an advantageous embodiment, the present method uses in-gel digests, and the analysis can then be performed without clean up. However, it is possible to digest the polypeptide either enzymatically or chemically, preferably enzymatically. It is most most preferable to utilize a digestion procedure which yields a basic or hydrophobic residue, most preferably a basic, at or near the C-terminus of the resulting peptides.

A polypeptide may be digested enzymatically e.g. using trypsin, endoproteinase Lys C, endoproteinase Arg C, or chymotrypsin. Trypsin, endoproteinase Lys C or endoproteinase Arg C are preferred, since the resulting peptides of the polypeptide will typically terminate at the C-terminus with an arginine or lysine residue (basic residue), with the exception of course of the C-terminus of the polypeptide. Other enzymes can be used, especially if basic residues occur at or near the C-terminus of the resulting peptides. For example, chymotrypsin, which typically cleaves at hydrophobic amino acid residues, may be used. Alternatively, chemical digestion can be used, such as by cyanogen bromide. (For a general reference to digestion methods, see e.g. U.S. Pat. No. 5,821,063.)

Thus, in a specific embodiment, the present method is used to identify a polypeptide or a protein, in which case a first step is included wherein said polypeptide or protein is digested, preferably enzymatically, to provide peptides. In a preferred embodiment, the enzyme is trypsin.

In an especially advantageous embodiment, the present method also includes a step of protecting specific residues before the derivatization step. For example, in a case where a polypeptide or protein is digested by trypsin, Lys residues will need to be protected in order to avoid e.g. undesired sulfonation reactions. An example of such a protection procedure by guanidination will be described in detail below in the experimental section (see example 5). Guanidination is advantageously used, since it is capable of selectively protecting Lys side chains without having any adverse effect on peptide recovery in subsequent steps such as mapping experiments. Furthermore, since such resulting modified lysine residues are susceptible to digestion, lysine terminated peptides can be used for a quantitative analysis.

The present method is preferably used with polypeptides from protein digests. Polypeptides can be used which preferably includes less than about 50 amino acid residues, more preferably less than about forty residues, even more preferably less than about thirty residues, still more preferably less than about twenty residues and most preferably less than about ten amino acid residues.

A second aspect of the present invention is the chemical compound 3-sulfopropionic acid N-hydroxysuccinimide ester as such, which is especially useful as a reagent for peptide derivatization, as discussed above.

A third aspect of the present invention is the chemical compound 2-sulfobenzoic acid N-hydroxysuccinimide ester as such, which is also useful as a reagent for peptide derivatization, as discussed above.

A fourth aspect of the invention is a kit for identifying a polypeptide, which kit contains an acidic reagent comprising a sulfonyl moiety coupled to an activated acid moiety in a suitable container. Such a kit can also comprise a model peptide.-The kit can also be accompanied by written instructions, e.g. in the form of a booklet, as to the use thereof.

Thus, in one embodiment, the present kit contains the necessary devices and means for performing a method of identifying a peptide or polypeptide according to the invention. A specific embodiment is a kit which comprises one or more of the novel reagents according to the invention and further means necessary for use with matrix-assisted laser desorption ionization time of flight (MALDI-TOF) mass spectrometry. An alternative embodiment is a kit which comprises one or more of the novel reagents according to the invention and further means necessary for use with electrospray ionization mass spectrometry (ESI-MS).

A fifth aspect of the present invention is the use of an acidic reagent comprising a sulfonyl moiety coupled to an ester moiety, such as an N-hydroxysuccinimide (NHS) ester, e.g. a 3-sulfopropionic acid N-hydroxysuccinimide ester or a 2-sulfobenzoic acid N-hydroxysuccinimide ester, as a derivatization reagent in a mass spectrometric technique. More specifically, the present invention relates to the use of the above described reagent in a method according to the invention.

DETAILED DESCRIPTION OF THE DRAWINGS

Figure 1B:
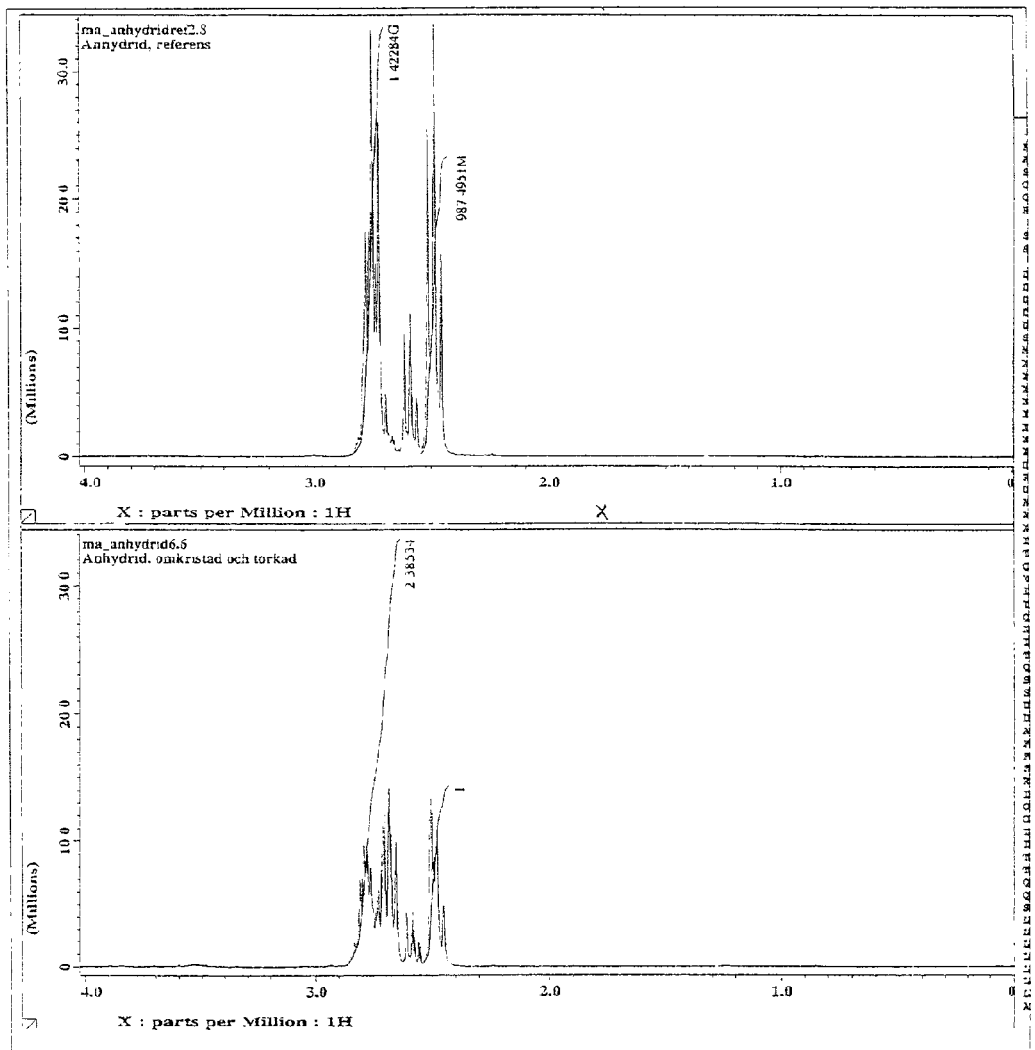
Figure 1C:
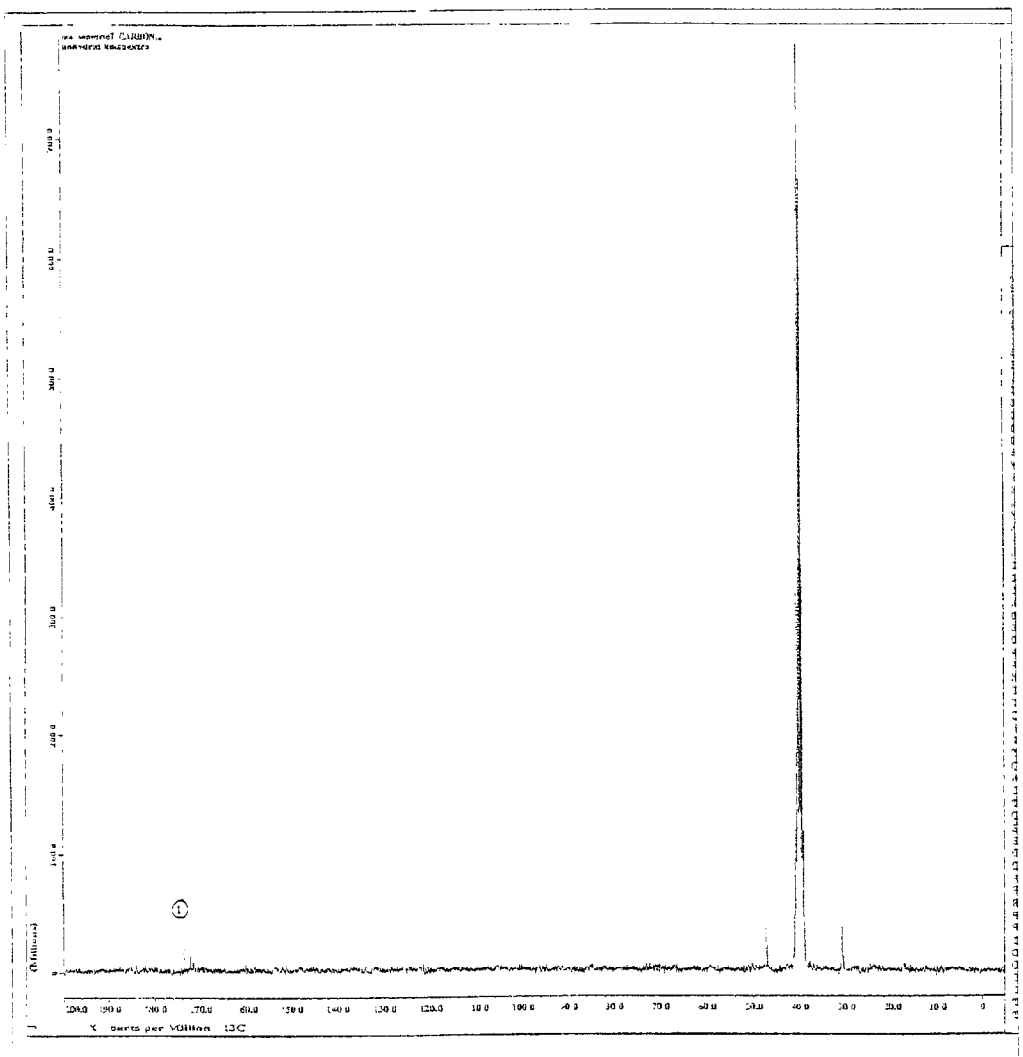
Figure 1D:
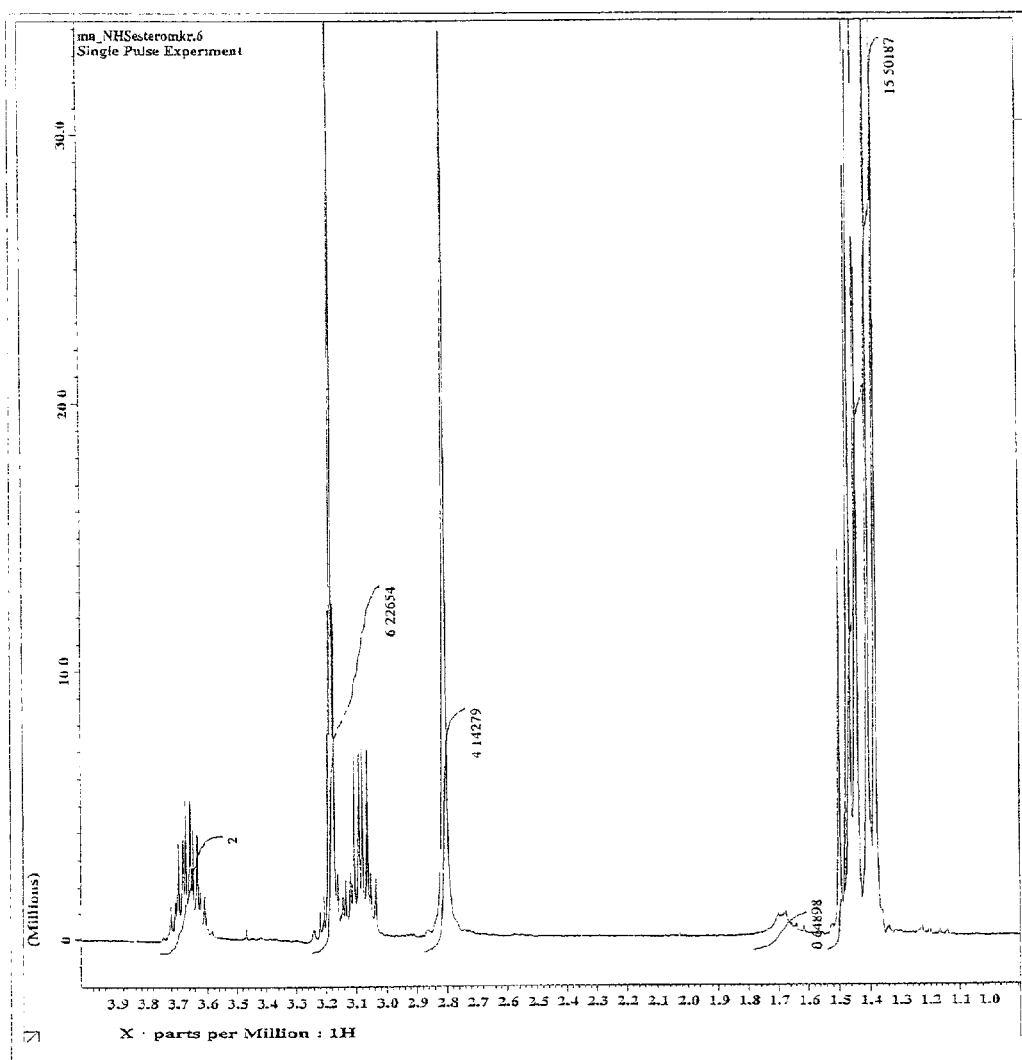

FIG. 1A–D show NMR-spectra as discussed in example 1 below. More specifically, FIG. 1A shows the spectrum of 3-sulfopropionic acid; FIG. 1B shows the $^{13}$C NMR spectrum of 3-sulfopropionic anhydride, FIG. 1C shows an anhydride carbon spectrum; and FIG. 1D shows the spectrum of the NHS-ester from 3-sulfopropionic anhydride.

Figure 2A:
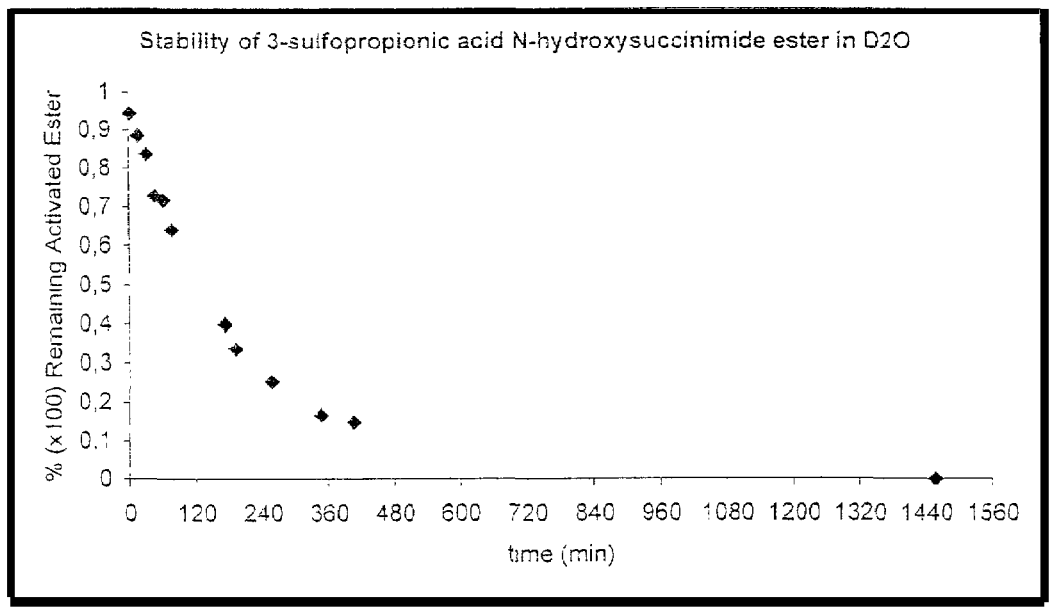
FIG. 2A–B illustrate the stability of NHS-esters according to the invention. More specifically.
Figure 2B:
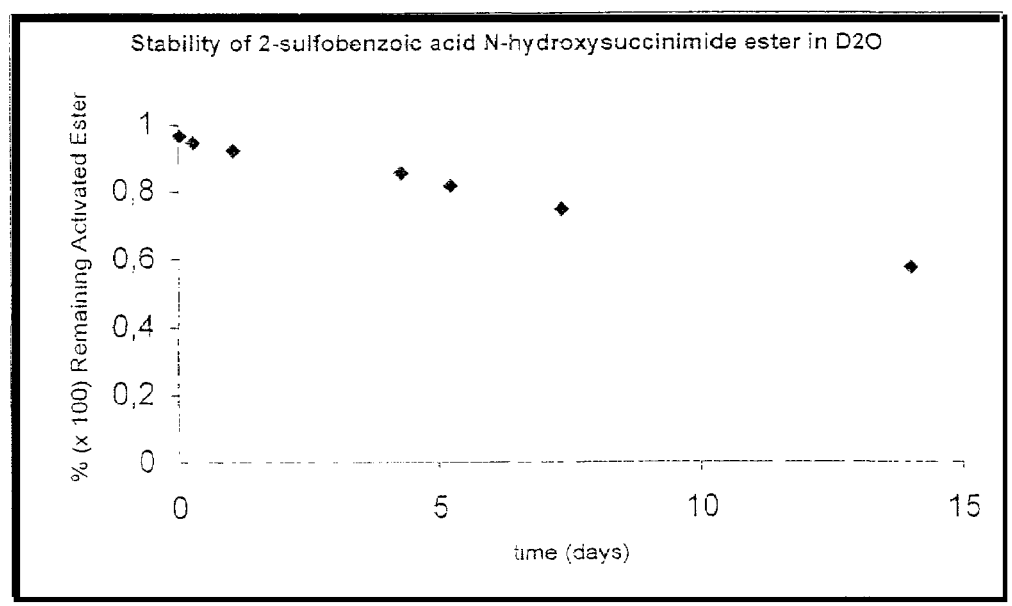

FIG. 2A–B illustrate the stability of NHS-esters according to the invention. More specifically, FIG. 2A shows the stability of 3-sulfopropionic acid NHS-ester in $D_2O$ while FIG. 2B shows the stability of 2-sulfobenzoic acid NHS-ester in $D_2O$. The analysis was conducted on a 270 MHz NMR-instrument from JEOL. NHS-ester were put in a NMR-tube and diluted with $D_2O$ to 700 µl. A single-pulse $^1$H-NMR was conducted and the spectra analysed. The hydrolysis being measured by the ratio of the integration of the signal at 2,92 ppm for 3-sulfopropionic acid N-hyrdoxysuccinimide, 3,01 ppm 2-sulfobenzoic acid N-hydroxysuccinimide and the signals of the protons of N-hydroxysuccinimide 2,76 ppm.

Figure 3A:
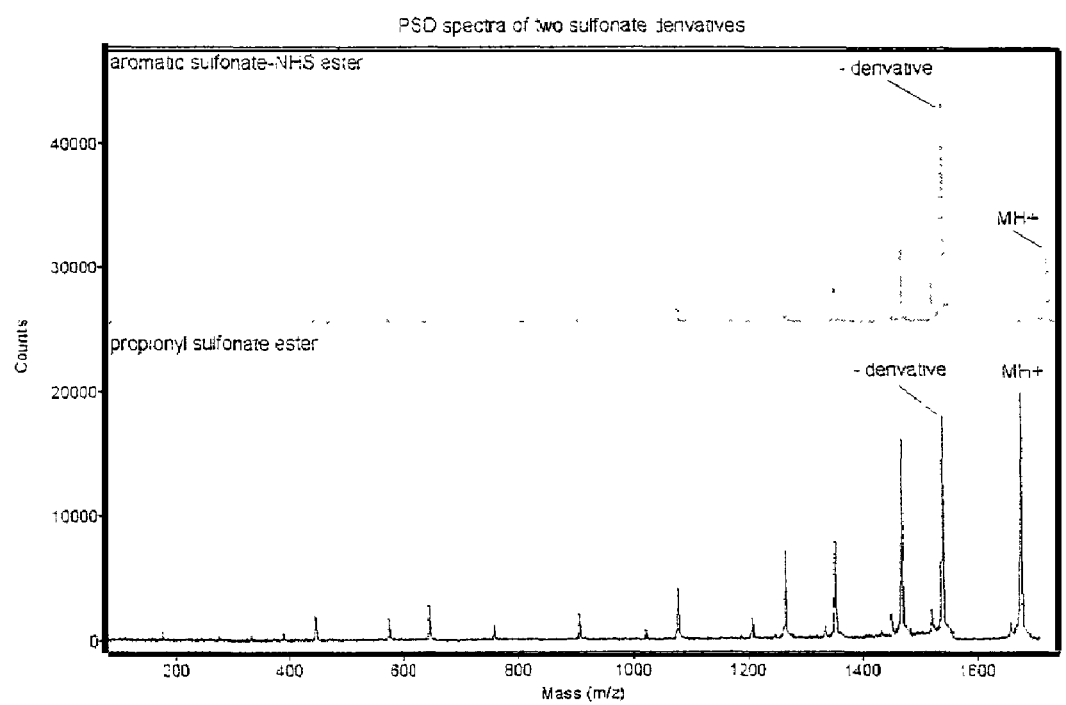
FIG. 3A–C show MALDI PSD spectra and comparative reactivity data of peptides sulfonated as described in Example 6.
Figure 3B:
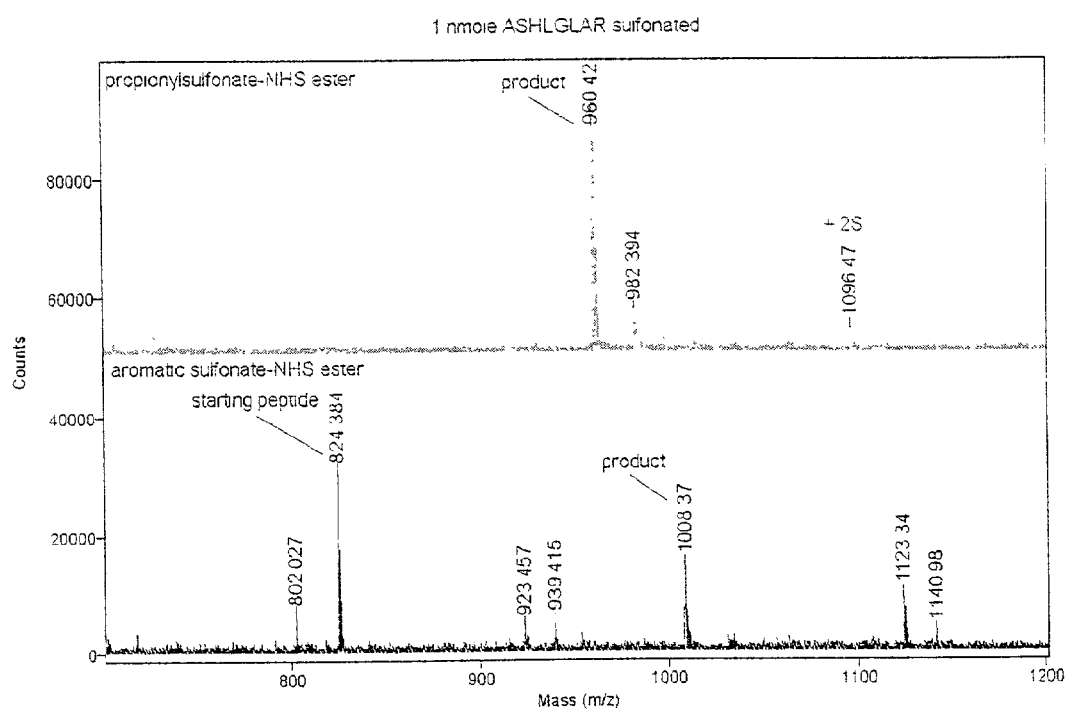
Figure 3C:
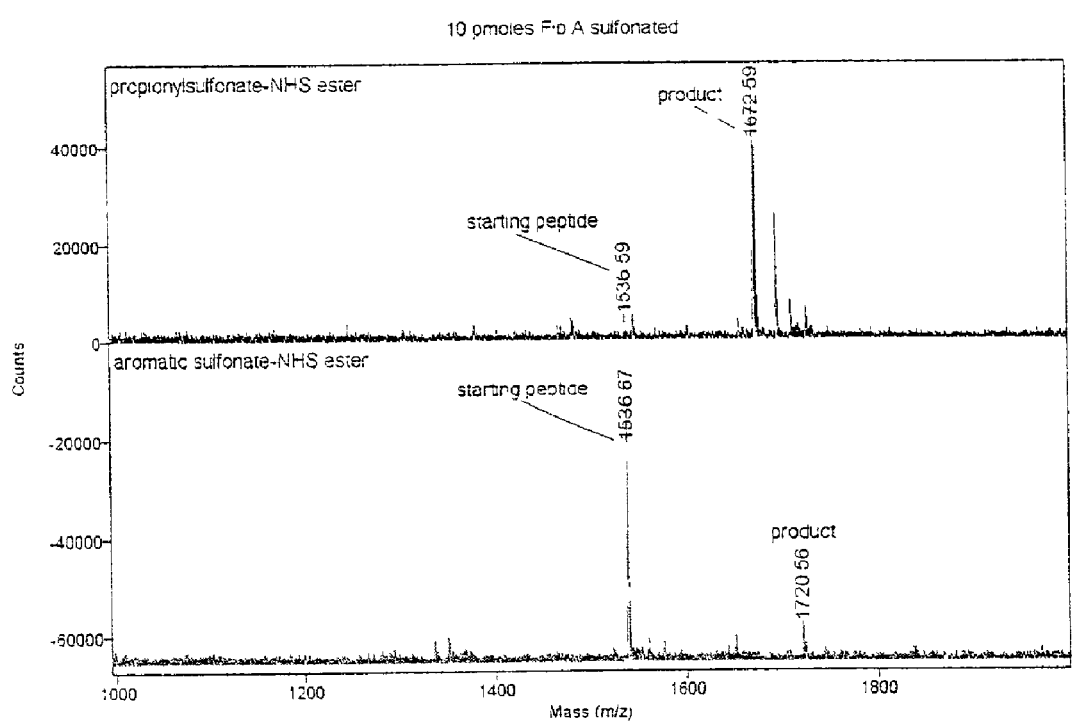

FIG. 3A–C show the MALDI PSD mass spectra produced from these derivatives and the comparative reactivities of peptides sulfonated as described in Example 4. More specifically, FIG. 3A shows a comparison of the fragmentation patterns produced from peptides containing 2-sulfobenzoic acetamides (upper) and 3-sulfopropionamides (lower). 3-Sulfopropionamides are preferred because of less loss of the derivative (which regenerates the starting peptide and is uninformative) and better yields of lower mass fragments, FIG. 3B shows a comparison of the reactivities of propionyl sulfonate NHS ester (upper) and the 2-sulfobenoic acid NHS ester (lower) with 1 nMole of a model peptide. The 3-sulfopropionic acid NHS ester shows better conversion of starting peptide to final product, and FIG. 3C is as in FIG. 3B but the reaction used 10 pmoles of FibA as the model peptide.

Figure 4:
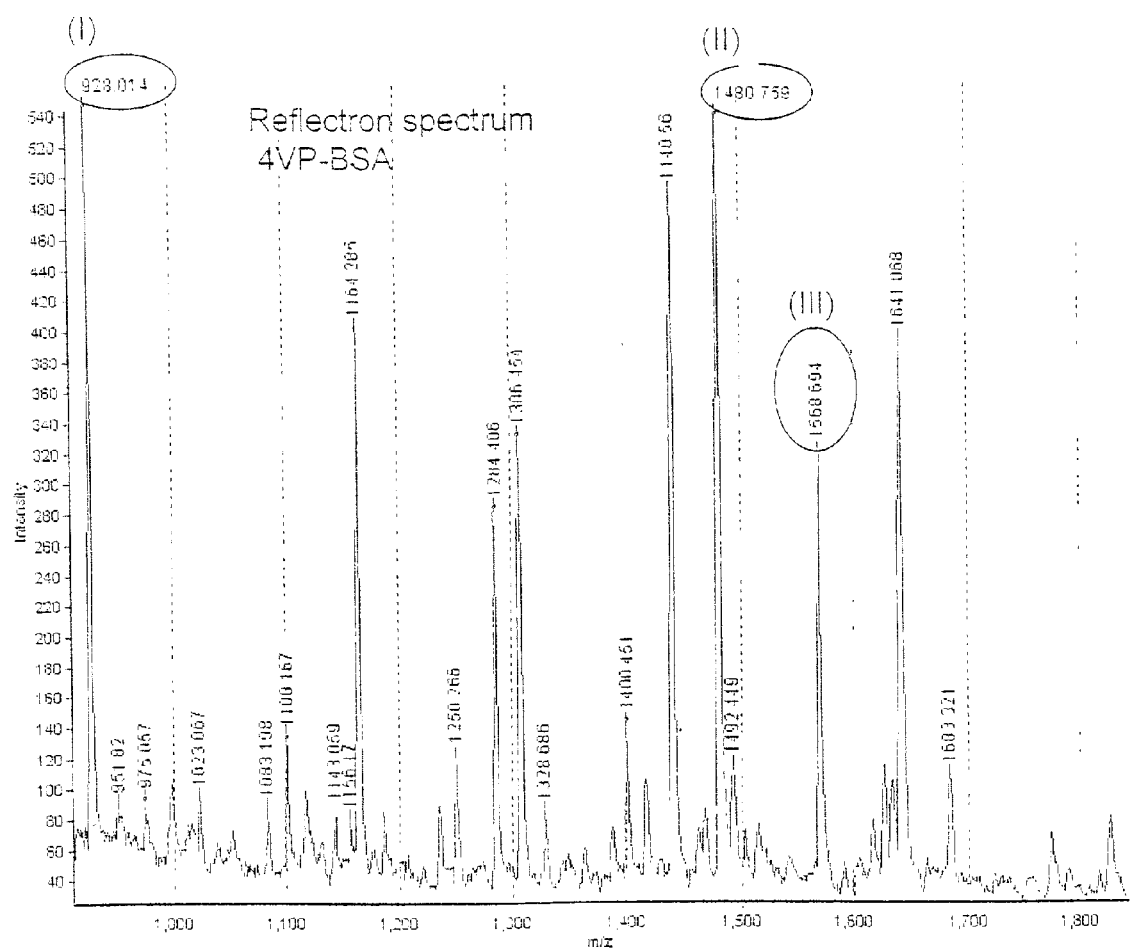
FIG. 4 shows a reflectron spectrum, positive mode (showing average masses, after filtration, smoothing 5) of non-derivatized tryptic digest of 4VP-BSA obtained with the Ettan™MALDI-TOF.

FIG. 4 shows reflectron spectrum, positive mode (showing average masses, after filtration, smoothing 5) of 250 fmol non-derivatized tryptic digest of 4VP-BSA obtained with the Ettan™MALDI-TOF. (Peptides I–III were quantitatively derivatized after reaction with 3-sulfopropionic acid anhydride NHS-ester, see FIG. 5).

Figure 5:
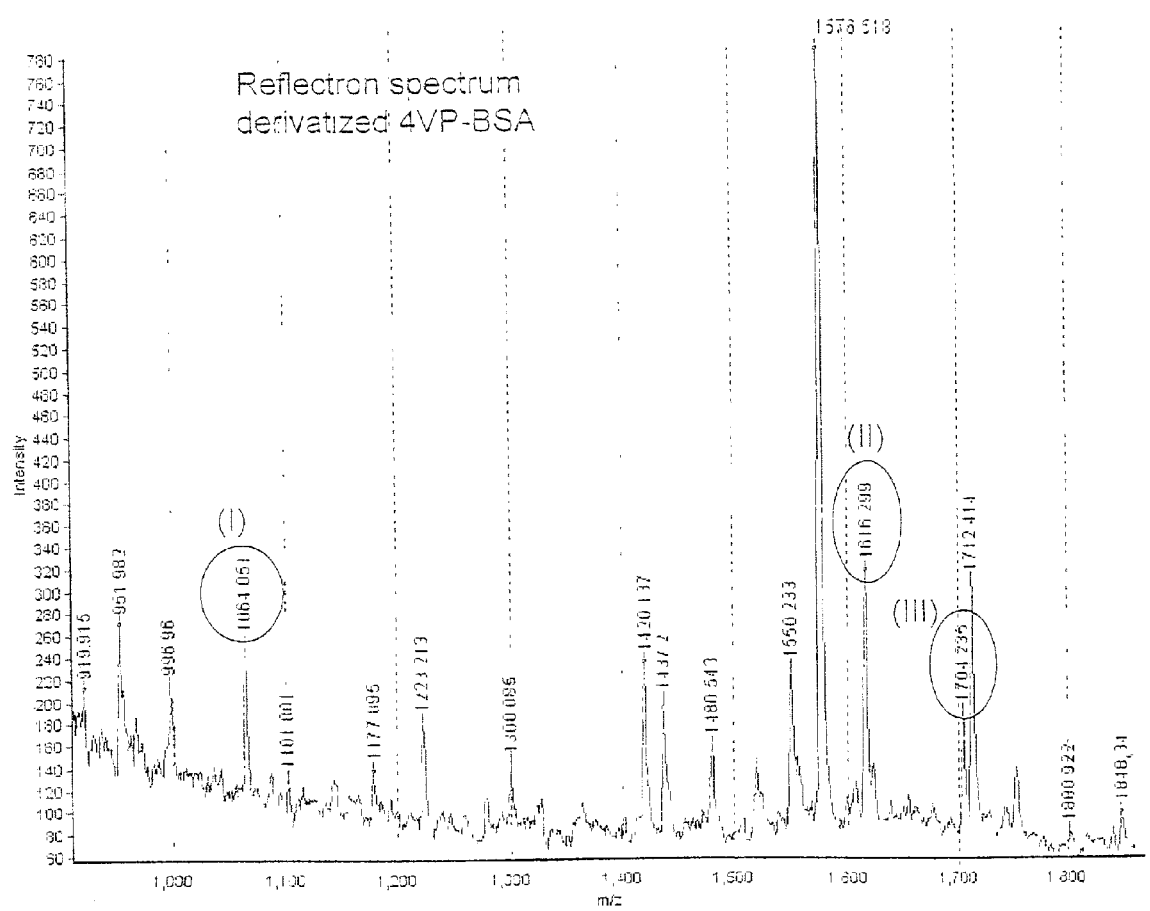
FIG. 5 shows a reflectron spectrum (showing average masses, after filtration, smoothing 5) of derivatized tryptic digest of 4VP-BSA (Ettan MALDI-TOF™).

FIG. 5 shows reflectron spectrum (showing average masses, after filtration, smoothing 5) of derivatized tryptic digest of 4VP-BSA (Ettan MALDI-ToF™). The peptides were derivatized with 3-sulfopropionic acid NHS ester under aqueous conditions as described. The peptides marked I–III were quantitatively derivatized and used for PSD analyses.

Figure 6:
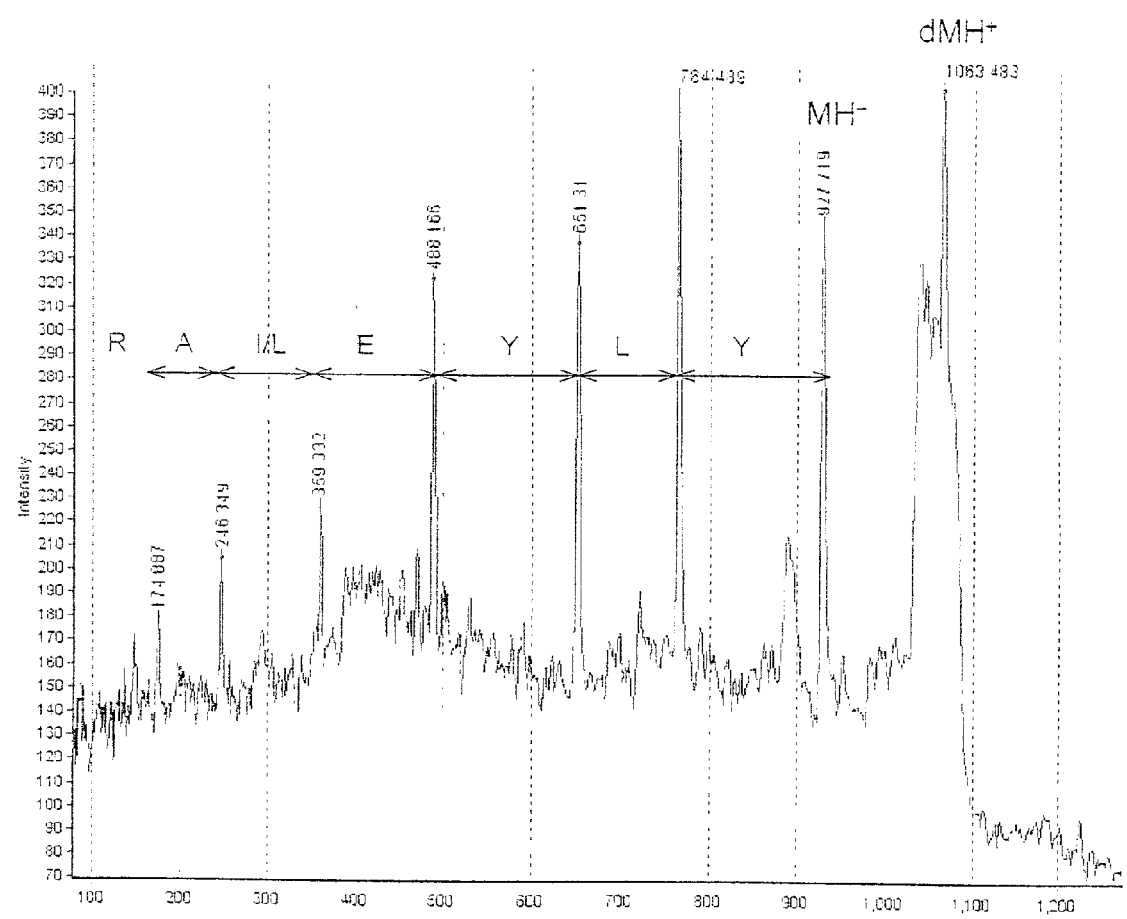
FIG. 6 shows fragmentation spectrum (PSD, positive mode) showing a complete Y-ion series of peptide (I) from the derivatized tryptic digest of 4VP-BSA (FIG. 5) obtained with the Ettan™MALDI-TOF.

FIG. 6 shows fragmentation spectrum (PSD, positive mode) showing a complete Y-ion series of peptide (I) from the derivatized tryptic digest of 4VP-BSA (FIG. 5) obtained with the Ettan™MALDI-TOF. The ion gate was set on the mass of the derivatized parent ion, m/z:1064, and the signals from 300 shots were accumulated.

Figure 7:
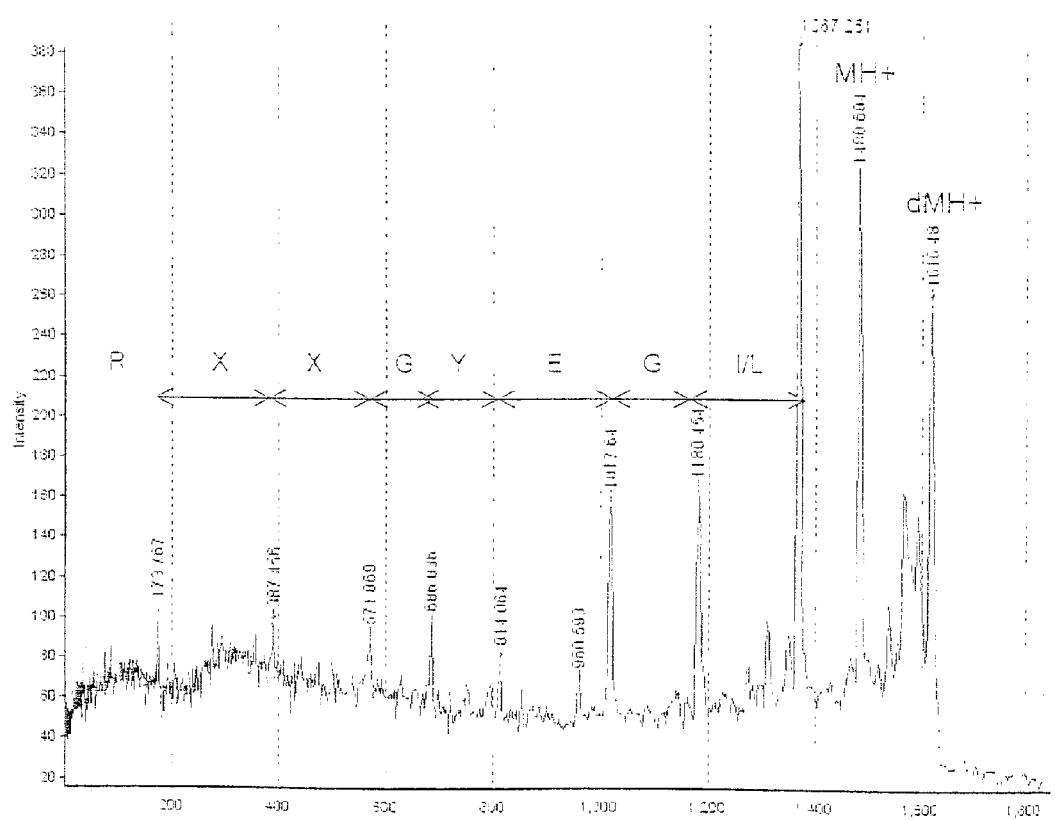
FIG. 7 shows fragmentation spectrum (PSD, positive mode) of peptide (II) from the derivatized tryptic digest of 4VP-BSA (FIG. 5).

FIG. 7 shows fragmentation spectrum (PSD, positive mode) of peptide (II) from the derivatized tryptic digest of 4VP-BSA (FIG. 5). The ion gate was here set on m/z:1616. Signals from 300 shots were accumulated. Gaps are marked with an X.

Figure 8:
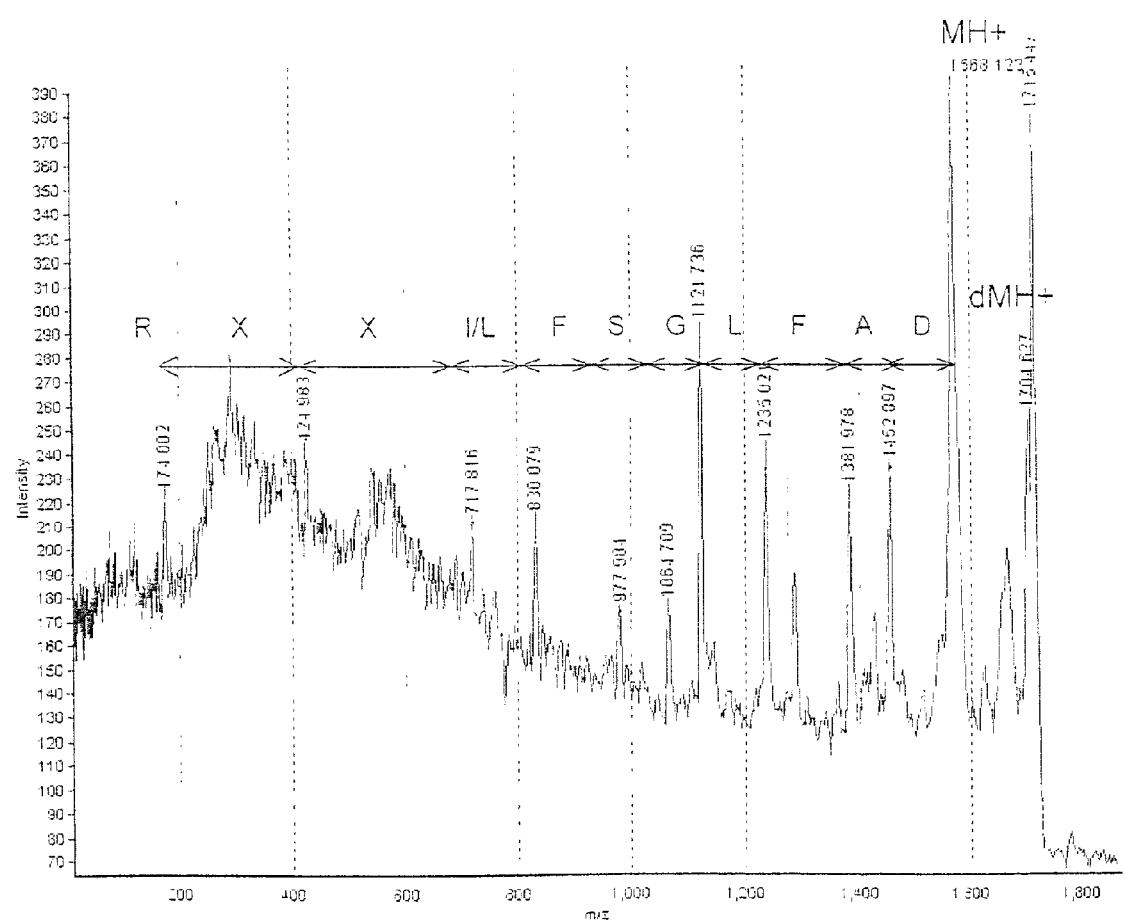
FIG. 8 shows PSD spectrum (signals from 300 shots accumulated) of peptide (III) (FIG. 5), m/z1704, from the derivatized tryptic digest of 4VP-BSA.

FIG. 8 shows PSD spectrum (signals from 300 shots accumulated) of peptide (III) (FIG. 5), m/z 1704, from the derivatized tryptic digest of 4VP-BSA. Gaps are marked with an X. The peptide, MH+ m/z 1715, passed the ion gate together with derivatized peptide.

Figure 9:
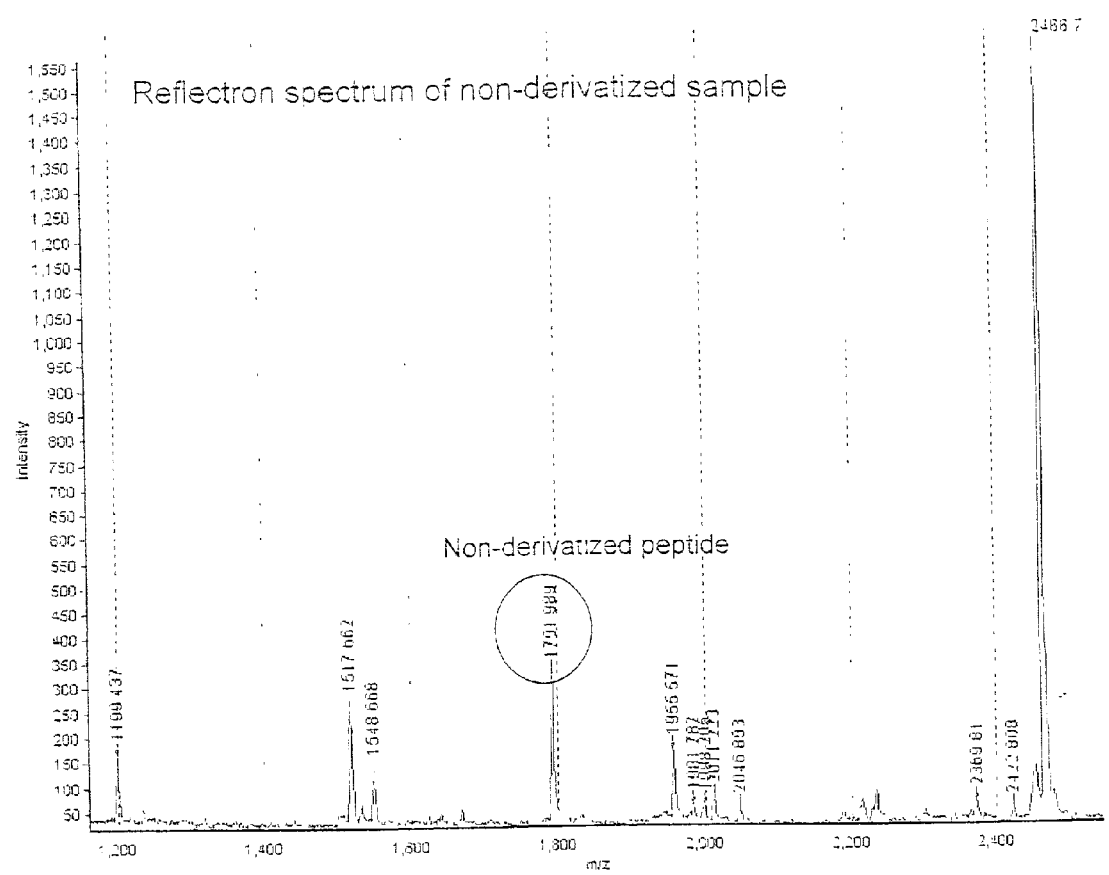
FIG. 9 shows a first example of a reflectron spectrum (positive mode, 100 shots accumulated, showing average masses, after filtration, smoothing 5) of a non-derivatized protein from a Coomassie-stained 2-D gel obtained with the Ettan MALDI-TOF.

FIG. 9 shows a first example of a reflectron spectrum (positive mode, 100 shots accumulated, showing average masses, after filtration, smoothing 5) of a non-derivatized protein from a Coomassie-stained 2-D gel obtained with the Ettan MALDI-TOF. Five percent of the total eluted tryptic digest was used to obtain this spectrum. (The peak marked with a circle can be seen fully derivatized in FIG. 10.)

Figure 10:
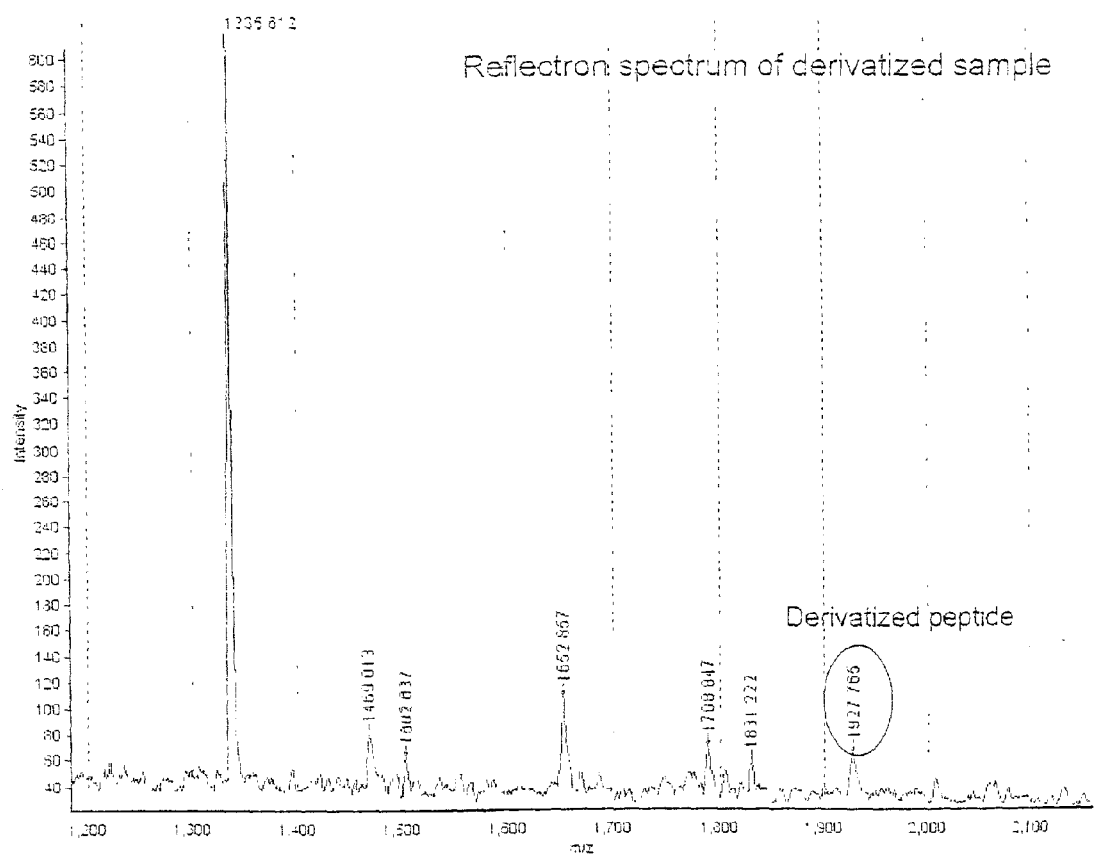
FIG. 10 shows a reflectron spectrum (positive mode, showing average masses, after filtration, smoothing 5) of the same 2-D sample as in FIG. 9 (remaining 95%), but after N-terminal derivatization with NHS-ester.

FIG. 10 shows a reflectron spectrum (positive mode, showing average masses, after filtration, smoothing 5) of the same 2-D sample as in FIG. 9 (remaining 95%), but after N-terminal derivatization with NHS-ester. The sample was cleaned up on a $\mu C_{18}$Zip Tip, and derivatized according the protocol. The peptide m/z 1791 (previous figure) was quantitatively derivatized and is here observed with the extra mass of the label, m/z 1927.

Figure 11:
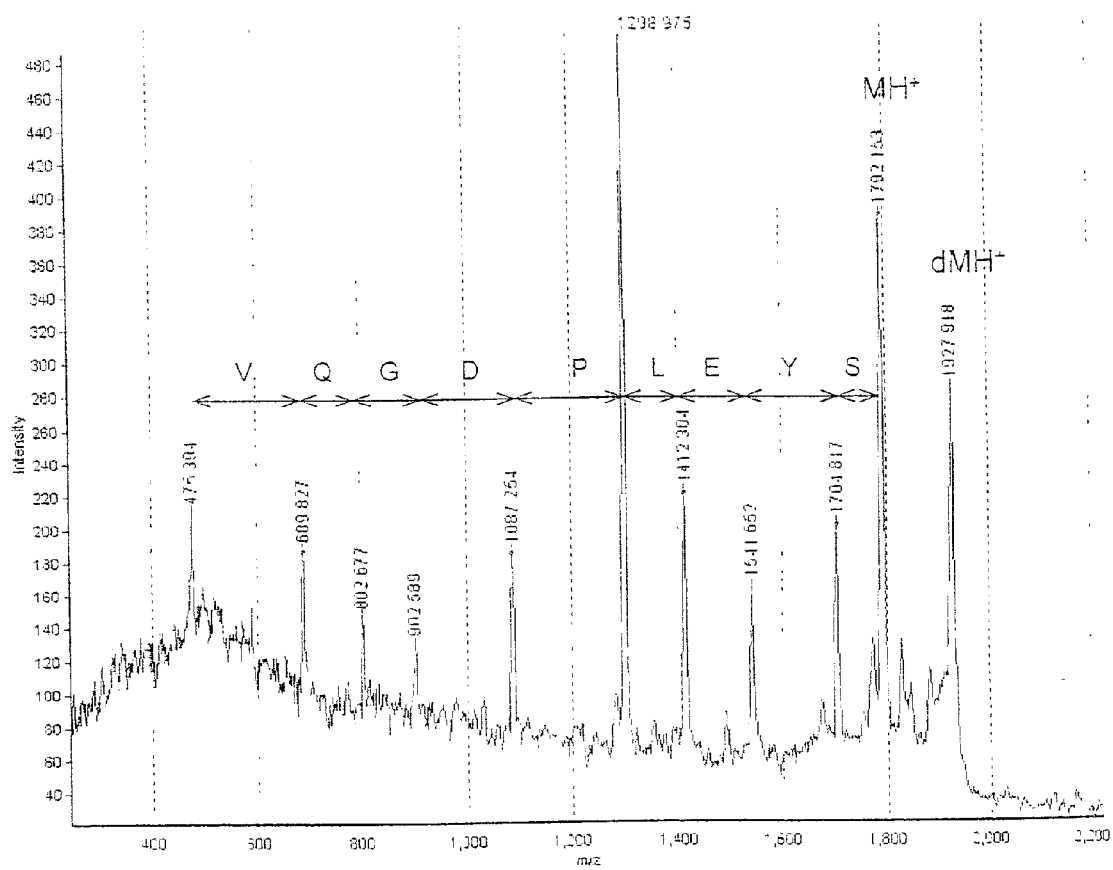
FIG. 11 shows a PSD spectrum (accumulated from 300 shots), of the derivatized peptide, m/z 1927.

FIG. 11 shows a PSD spectrum (accumulated from 300 shots), of the derivatized peptide, m/z 1927. The masses of the fragments (y-ions) were used for identification in PepFrag. The protein was identified as actin.

Figure 12:
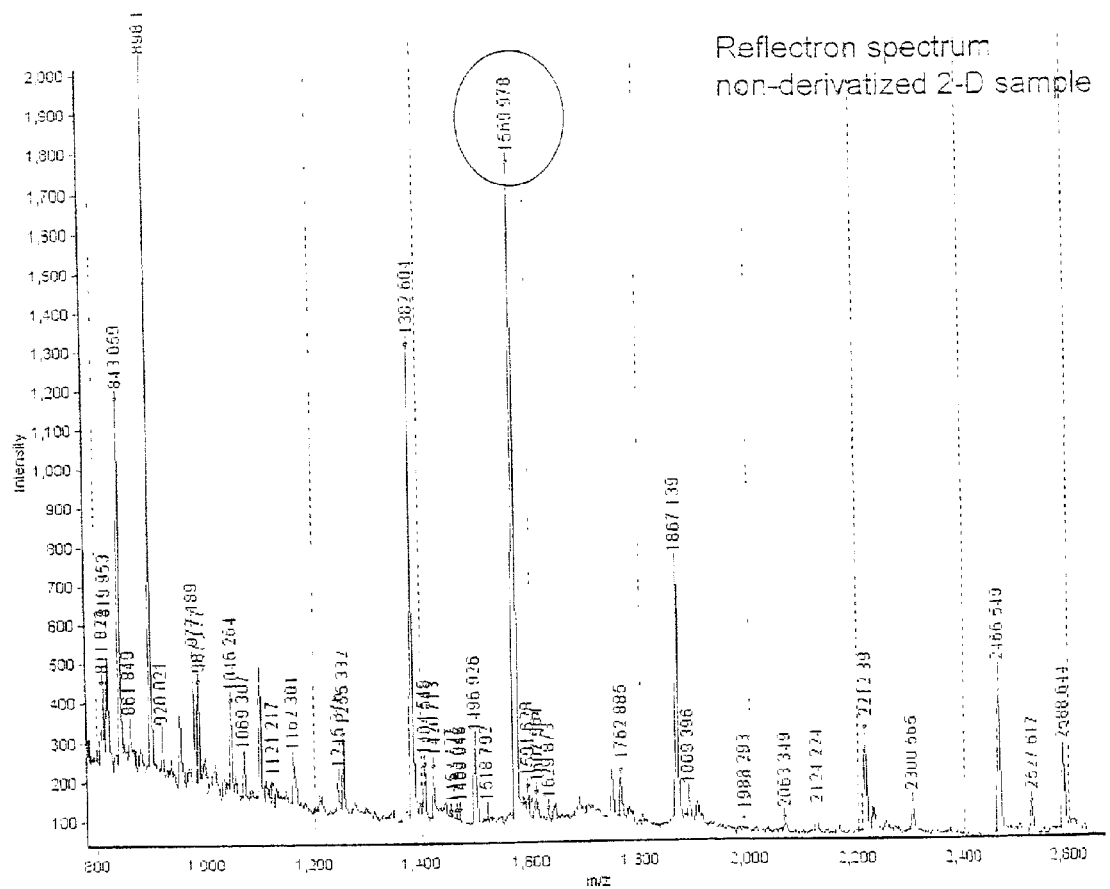
FIG. 12 shows a second example of a reflectron spectrum (accumulated from 100 shots, showing average masses, after filtration, smoothing 5) of a non-derivatized tryptic digest of a protein spot from a Coomassie-stained 2-D gel, obtained with Ettan™MALDI-TOF.

FIG. 12 shows a second example of a reflectron spectrum (accumulated from 100 shots, showing average masses, after filtration, smoothing 5) of a non-derivatized tryptic digest of a protein spot from a Coomassie-stained 2-D gel, obtained with Ettan™MALDI-TOF. Five percent of the sample was used in this analysis. The marked peptide was used for PSD analyses after derivatization (see next figure).

Figure 13:
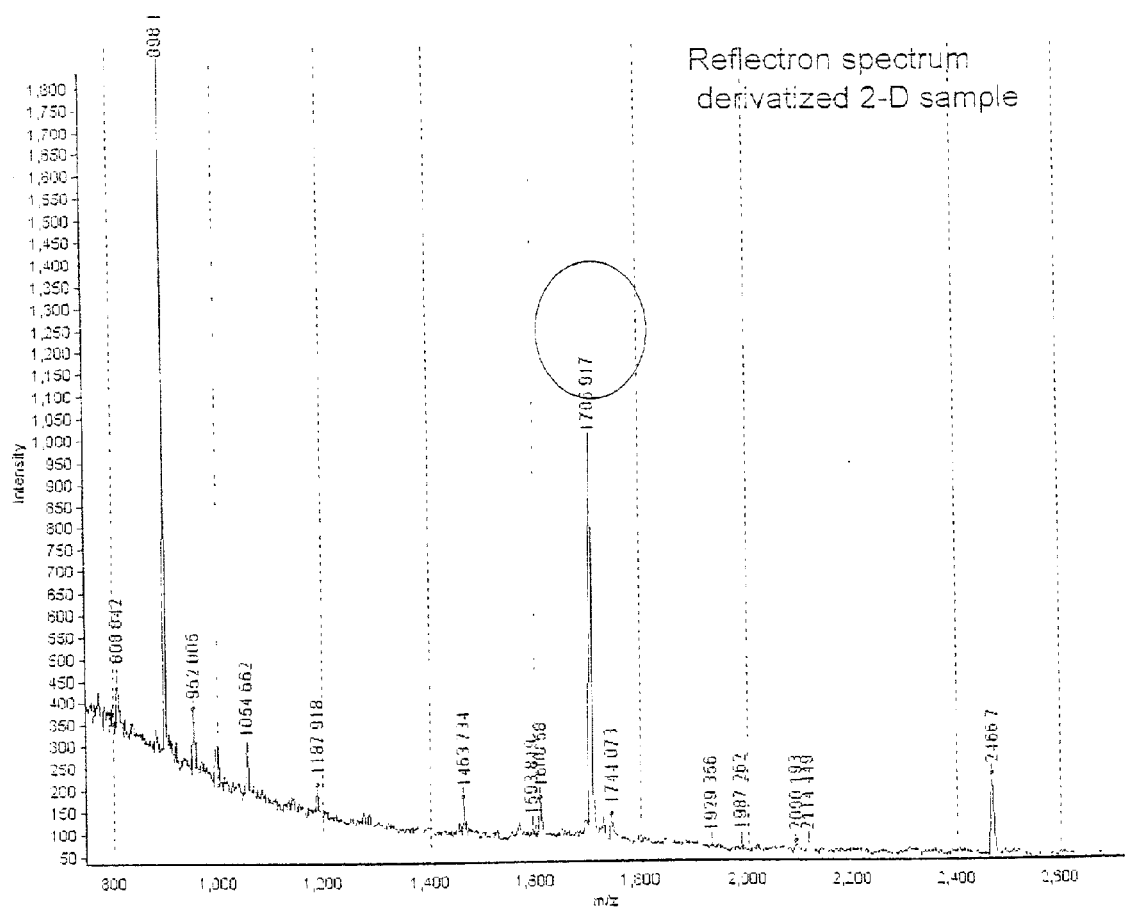
FIG. 13 shows a reflectron spectrum (positive mode showing average masses, after filtration, smoothing 5) of the same 2-D sample as in FIG. 11, but after Zip Tip clean up and derivatization with NHS-ester in aqueous solution as described.

FIG. 13 shows a reflectron spectrum (positive mode showing average masses, after filtration, smoothing 5) of the same 2-D sample as in FIG. 11, but after Zip Tip clean up and derivatization with NHS-ester in aqueous solution as described. The peptide m/z 1569.9 (previous figure) was quantitatively derivatized and is here observed with the extra mass of the label (+136) as m/z 1705.9.

Figure 14:
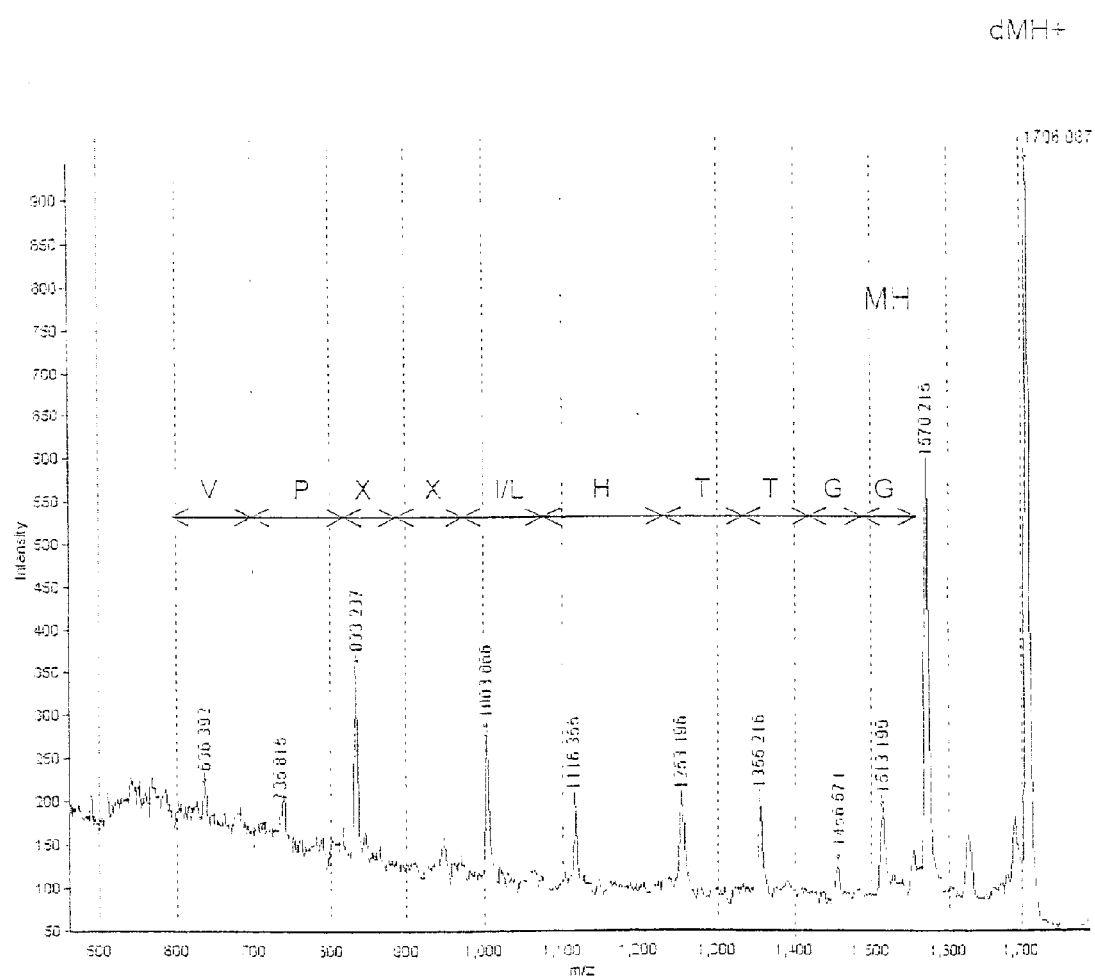
FIG. 14 shows a PSD spectrum (signal from 300 shots accumulated) of the derivatized peptide, m/z 1705 (see FIG. 12).

FIG. 14 shows a PSD spectrum (signal from 300 shots accumulated) of the derivatized peptide, m/z 1705 (see FIG. 12). The fragment masses (y-ions) were used for protein identification in PepFrag. The protein was identified as *E-coli* succinyl-CoA synthetase.

EXAMPLES

The present examples are intended for illustrative purposes only and should not be construed as limiting the invention as defined by the appended claims. All references given below and elsewhere in the present application are hereby included herein by reference.

Example 1

Preparation of 3-Sulfopropionic Acid N-hydroxysuccinimide Ester

Materials

Chemicals for Synthesis:
N-Hydroxysuccinimide (NHS), internal supply, Art-Nr 30070800
3-Mercaptopropionic acid from ALDRICH 99+%, CAS-107-96-0
Hydrogen peroxide (30%, aqueous solution)
Acetic acid (glacial) 100% from KEBO CAS-64-19-7
Potassium hydroxide from Merck, pellets
n-Heptane from Merck 99%
Thionyl chloride from ALDRICH 99+%, CAS-7719-09-7
n-Hexane from Merck 99%
Diisopropyl amine from ALDRICH 99%, CAS-7087-68-5
Dichloromethane from ALDRICH 99.8% anhydrous, CAS-75-09-2
Argon gas-tube from Air Liquide
Ethyl acetate from KEBO, CAS-141-78-6
Methanol from KEBO, CAS-67-56-1
TLC Silica gel 60 $F_{254}$ on plastic sheets from Merck Chemicals for Analysis:
Chloroform-d from Cambridge Isotope Laboratories 99.8%, CAS-865-49-6
Deuteriumoxide ($D_2O$) from Larodan Fine Chemicals CAS-7789-20-0

Methods

NMR-analysis:
The analysis was conducted on a 270 MHz NMR-instrument from JEOL.

10 mg of NHS-ester were put in a NMR-tube and diluted with $CDCl_3$ to 700µl. A single-pulse $^1$H-NMR was conducted and the spectra analysed. The analysis was conducted in the same way for 3-sulfopropionic anhydride. For the 3-sulfopropionic acid, $D_2O$ was used as a solvent instead of $CDCl_3$.

For the 3-sulfopropionic anhydride a decoupled $^{13}$C-NMR was carried out in the same way as with the $^1$H-NMR (see above).

Melting Point Determination:
The melting point for the NHS-ester crystals was obtained on a BÛCHI Melting Point B-540 apparatus. A few crystals were put in a vial and heated until they melted. The temperature interval was from 160° C. to 185° C. and the temperature gradient 1° C./min.

Stability Test in Water
10 mg of NHS-ester were put in a NMR-tube and 700µl of $D_2O$ was added. A single-pulse $^1$H-NMR was conducted and the spectra analysed. The same sample was stored at RT (20–25° C.) and after 5 and 24 hours another $^1$H-NMR spectra were collected.

Stability Test in Air:
10 mg of NHS-ester were put in a NMR Tube and analysed as above with Chloroform-D as solvent. About 100 mg of the NHS-ester were then put in a flask and kept without lid in air and RT (20–25° C.) for some days. The hydrolysis of the ester was followed with NMR.

Synthesis

Synthesis of 3-Sulfopropionic Acid

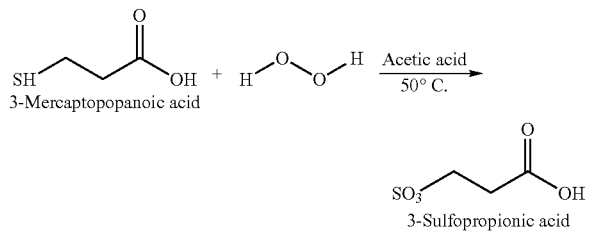

A 3-necked roundbottomed flask (500 ml) was equipped with a thermometer, dropping funnel and a degassing pipe. A gas-trap with two security-flasks (coupled in series after each other), the last containing 25% KOH-solution was fitted to the pipe During the reaction a nitrogen-balloon kept an inert atmosphere through the system. Acetic acid (70 ml) and hydrogen peroxide (70 g, 30% aqueous solution, 620 mmol) were put in the flask and the solution was heated under stirring to 50° C. on a waterbath. 3-Mercaptopropanoic acid (8,20 ml, 94 mmol) was added very carefully through the dropping funnel over a period of about 1 hour. An exothermic reaction started at once and the temperature rose to about 80° C. The solution was then cooled on an ethanol/$CO_2$ bath (−72° C.) until the temperature was again 50° C., this procedure was repeated until all the 3-mercaptopropanoic acid had been added from the dropping funnel. The reaction was then left stirring at 50° C. for two hours and at RT over night.

The solvent was evaporated on a rotaryevaporator (waterbath 40° C., 100 mbar) until the volume had been reduced to about 30 ml, the rest was then removed by azeotropic evaporation with 3×300 ml heptane. The resulting oil was dried in a desiccator under high vacuum over night. The crude product was a white precipitate in an oil. The yield was about 50%, estimated from the NMR-spectrum, see FIG. 1.

Synthesis of 3-sulfopropionic Anhydride:

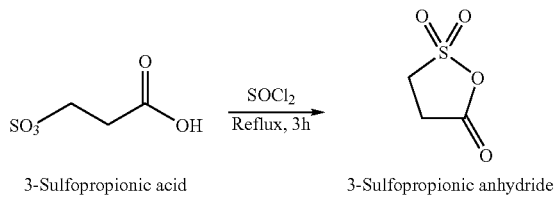

The 3-sulfopropionic acid (20 g of the crude product from the experiment above) was put in a 3-necked roundbottomed flask. A reflux-condenser and a septum were fitted to the flask. During magnetic stirring, $SOCl_2$ (140 ml) was carefully added through the septum over a period of 30 minutes. When all the $SOCl_2$ had been added the mixture was refluxed for 3 hours. Everything had dissolved during reflux into a brown-red coloured solution. After cooling for about 5 minutes, hexane (140 ml) was added. A white solid precipitated at once and a brown oil was formed at the bottom of the flask. The solution was then heated again until the white solid had dissolved and the solution was decanted into another flask to get rid of the oil. The solution was then allowed to cool in RT for an hour and then put in a refrigerator over the weekend for crystallisation.

The precipitate was filtered under nitrogen atmosphere, washed with cold n-hexane (from the refrigerator) and dried in a desiccator under high vacuum over night. All equipment that was used for the filtration had been dried in an oven beforehand and cooled in a desiccator, since the anhydride is very sensible to water.

Synthesis of NHS-Ester from 3-Sulfopropionic Anhdride:

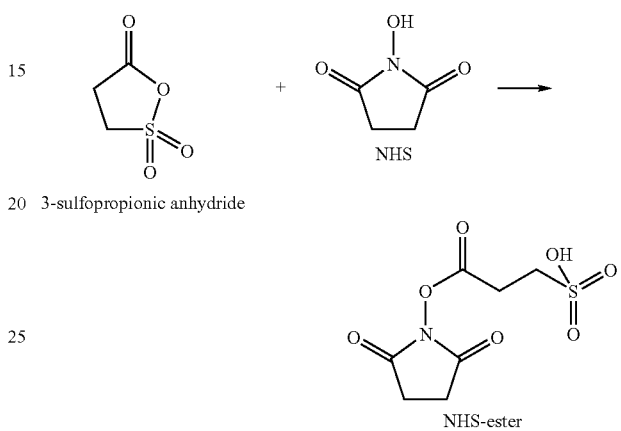

All equipment that was used was dried in an oven (100° C.) and put in a desiccator before the synthesis.

NHS (420 mg, 3,68 mmol) was weighed into a roundbottomed flask (100 ml) equipped with a septum and an argon balloon. DCM (20 ml, anhydrous 99.5%) was added and magnetic stirring began. DIEA (0.64 ml, 3,68 mmol) and 3-sulfopropionic anhydride (0.50 g, 3,68 mmol) were added carefully during stirring. The reaction was left stirring for three hours under an argon atmosphere. The solvent was evaporated (RT, 100 mbar) and the product was dried in a vacuum oven over night (RT, 1 mbar). The resulting crystals were dissolved in the minimum amount of warm EtOAc/MeOH (9:1). When everything had dissolved the solution was left to cool in RT for about three hours and then in the freezer over night. During the night white crystals had formed which were filtered on a glass filter (p3) and washed with cold ethyl acetate (5C.°). Finally the crystals were dried under high vacuum in a desiccator to get the DIEA-salt of the NHS-ester as white crystals (42% yield).

Results & Discussion

Synthesis

Synthesis of 3-Sulfopropionic Acid:

The synthesis was quite simple and gave the crude 3-sulfopropionic acid as a white slurry. The tricky part was to keep the reaction at 50° C., this was done with alternating ice-bath and oil-bath which perhaps is not the most effective way. The temperature during the reaction varied from 20 ° C. up to 80° C. If a better temperature control could be maintained under the reaction maybe the yield would improve. No further purification was done since it was not necessary for the next step (synthesis of the anhydride) making the yield very hard to calculate. On the NMR-spectra you could see at least one bi-product and maybe some of the starting material (see NMR-analysis) an estimation of the purity would be around 50%.

Synthesis of 3-sulfopropionic Anhydride:

As expected the anhydride was very sensitive to water and it was necessary to dry all equipment in an oven before use and to do the reaction and purification under an argon atmosphere. The reaction and recrystallisation was done in $SOCl_2$ which is a very toxic solvent. The product, 3-sulfopropionic anhydride, was collected as light-brown crystals. For a reliable calculation of the yield, it is essential that the starting material is pure.

Synthesis of NHS-ester from 3-sulfopropionic Anhydride:

Once again the materials were dried in an oven before the reaction which was done under an argon atmosphere. The reaction was quite simple and after two hours of stirring the solvent was evaporated to give the crude NHS-ester/DIEA-salt as a white/yellow solid. The yield after purification was 42%. A longer reaction time and excess NHS and/or DIEA could possibly improve the yield. The yield is also calculated on a 100% pure 3-sulfoprpionic anhydride.

Purification:

The crude NHS-ester/DIEA-salt was recristallized. This was done in EtOAc/MEOH (9:1) after first trying EtOAc/MeOH (7:3). The latter one gave no crystallisation after cooling.

In the synthesis of the anhydride (see above) a sort of recrystallisation was done in $SOCl_2$. This however was in reality just a re-heating of the reaction mixture and a decantation to get rid of the oil in the bottom of the flask. A better purity of the anhydride will be achieved by a proper recrystallisation.

Characterisation

Melting Point Determination:

The melting point of the crude NHS-ester/DIEA-salt was between 145–155° C. After recrystallisation however the melting point was determined to 176–178° C. This higher and much sharper melting point after purification indicates that the product has indeed become purer.

NMR-analysis:

The spectra obtained from NMR analysis is shown in FIG. 1.

3-sulfopropionic Acid:

TABLE 1

Interpretation of the $^1$H-NMR-spectra of 3-sulfopropionic acid $CDCl_3$

| Proton number | Shift (δ ppm) | Interpretation | Group |
|---|---|---|---|
| 1, 2 | 3.13 | t, methylene protons | $O_3S$—C$\underline{H}$2—CH2—COOH |
| 3, 4 | 2.75 | t, methylene protons | $CH_2$—C$\underline{H}$2—COOH |

The spectra also contained some by-product and some starting material giving some peaks at δ2.78, δ2.85, δ3.18 and at δ3.52. This was expected when no purification had been done.

3-Sulfopropionic Anhydride

TABLE 2

Interpretation of the $^1$H-NMR-spectra of 3-sulfopropionic anhydride $CDCl_3$

| Proton number | Shift (δ ppm) | Interpretation | Group |
|---|---|---|---|
| 1, 2, 3, 4 | 2.45–2.85 | m, methylene protons | $—O_3S—C\underline{H}2—C\underline{H}2—COO—$ |

TABLE 3

Interpretation of the decoupled $^{13}$C-NMR -spectra of 3-sulfopropionic acid $CDCl_3$

| Carbon number | shift (δ ppm) | Interpretation | Group |
|---|---|---|---|
| 1 | 47 | Alkyl carbon | $O_3S$—$\underline{C}$H2—CH2—COOH |
| 2 | 31 | Alkyl carbon | $O_3S$—$CH_2$—$\underline{C}$H2—COOH |
| 3 | 174 | Carbonyl carbon | $O_3S$—$CH_2$—CH2—$\underline{COOH}$ |

Both spectra were compared and confirmed with reference spectra.

NHS-ester from 3-propionic Anhydride:

TABLE 4

Interpretation of the $^1$H-NMR-spectra in $CDCl_3$

| Proton number | Shift (δ ppm) | Interpretation | Group |
|---|---|---|---|
| 1, 2 | 3.20 | m, methylene protons | $O_3S$—C$\underline{H}$2—CH2—COO— |
| 3, 4 | 3.08 | m, methylene protons | $O_3S$—CH2—C$\underline{H}$2—COO— |
| 5, 6, 7, 8 | 2.80 | s, methylene protons | —CO—C$\underline{H}$2—C$\underline{H}$2—CO— |
| DIEA (2 protons) | 3.67 | m, methine protons | $(CH3)_2$C$\underline{H}$—N(C2H5)—C$\underline{H}$(CH3)$_2$ |
| DIEA (2 protons) | 3.20 | m, methylene protons | —N—C$\underline{H}$2—CH3 |
| DIEA (15 protons) | 1.40 | dd, methyl protons | $((C\underline{H}3)_2$—CH)$_2$N—CH2—C$\underline{H}$3 |

Typical inpurities in the crude product are NHS and DIEA. NHS gives a peak at δ2.68(s) and DIEA gives peaks at almost the same ppm as seen above in the table. This makes the DIEA impurity harder to spot than NHS but it can be estimated by looking at the integral of the peaks. If there are any solvent left the MeOH gives a peak at δ3.49(s), EtOAc at δ2.05(s), δ1.26(t) and at δ4.12(q) and finally DCM at δ5.30(s).

Example 2

Preparation of 2-sulfobenzoic Acid N-hydroxysuccinimide Ester

The N-hydroxysuccinimide (NHS) ester of 2-sulfo benzoic cyclic anhydride was prepared as DIPEA salt according to scheme 3 and as explained below:

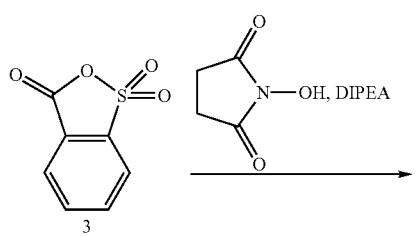

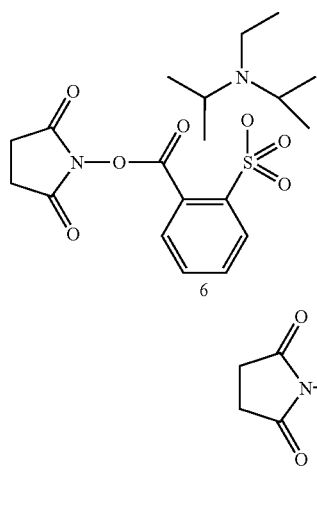

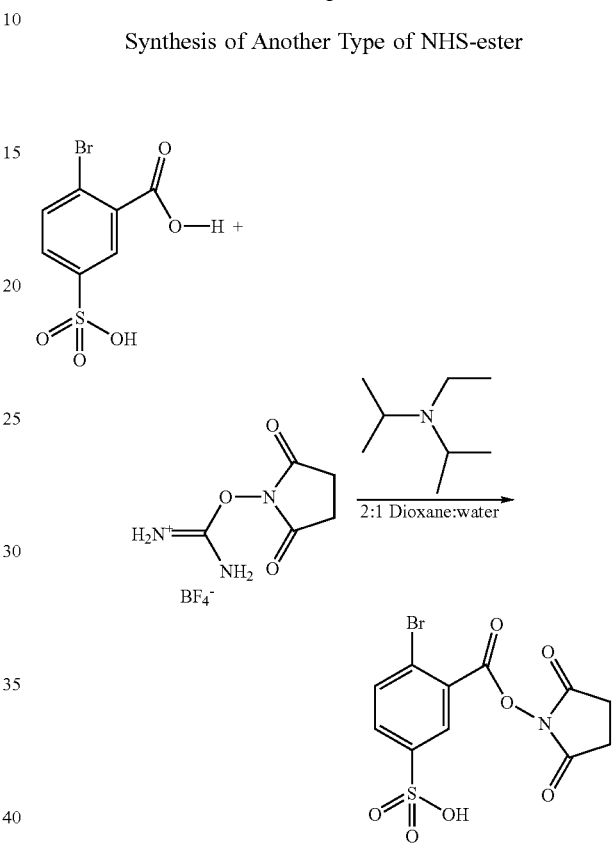

All equipment was dried in an oven and transferred in an exiccator filled with argon prior to use. The reaction was carried out under an argon atmosphere. NHS and 2-sulfo benzoic acid cyclic anhydride were dried under vacuum prior to use.

Methylene chloride (1.9 ml) and DIEA (1.019 ml, 5.85 mmol) were added to a round bottle flask containing NHS (673.2, 5.85 mmol). A solution of 2-sulfo benzoic acid cyclic anhydride (1.077 g, 5.85 mmol) in methylene chloride (19 ml) was then added in portions (7×) to the reaction mixture, which was then left at room temperature for 2 h 20 min. The reaction mixture was split in two parts, which were evaporated to give a light yellow highly viscous residue (1. 1.11 g and 2. 1.24 g, respectively).

Fraction 1 was dissolved in MQ (11.098 ml, 100 mg/ml), filtered and used 3×1 ml in reversed phase preparative HPLC; Column: Supelcosil LC-18, 10 cm×21.2 mm, 2μ; Flow: 10 ml/min, Method: 0–10 min. isocratic 5% acetonitrile containing 0.1% TFA B in water, 2 min. sample injection, 10–15 min. Gradient 5–12% B in water. The fractions were evaporated and freeze dried to give a white solid/transparent viscous oil (totally 237.7 mg) of not purified product in DIEA salt form, NHS, DIEA and side product. A previous more successful attempt using reversed phase preparative HPLC with the same column and system but another method: 0–6 min. isocratic 5% acetonitrile containing 0.1% TFA B in water, 2 min. sample injection, 6–18 min. Gradient 5–25% B in water, resulted in the product as a DIEA salt with approximately 5% NHS left and some traces from side-product in the aromatic area.

$H^1$ NMR (D$_2$O) δ:8.0–8.1 (dd, 1H) 7.9–8.0 (dd, 1H) 7.7–7.8 (m, 2H) 3.6–3.8 (m, 2H) 3.1–3.2 (m, 2H) 3.0 (s, 4H) 1.2–1.3 (m, 15 H) and 2.7 (s, 0.2 H, NHS peak).

Acetone (2.5 ml cold, 0° C., ice-water bath) was added to fraction 2 dropwise to give a white precipitation after 20 min. in room temperature and 25 min. in 4° C. The precipitate was filtered and washed carefully in acetone (24 ml cold, 00C, ice-water bath) to give the product as a DIEA salt (612.7 mg, 46.3%).

$H^1$ NMR (D$_2$O) δ:8.0–8.1 (dd, 1H) 7.9–8.0 (dd, 1H) 7.7–7.8 (m, 2H) 3.6–3.8 (m, 2H) 3.1–3.3 (m, 2H) 3.0 (s, 4H) 1.2–1.3 (m, 15 H).

Example 3

Synthesis of Another Type of NHS-ester 2-bromo-5-sulfobenzoic acid is dissolved in 1 mL dioxane and 0.5 mL water. The diisopropylethylamine, 2 eq., is added. To this well stirred solution is added the O-(N-Succinimidyl)-N,N,N',N'-tetramethyluronium BF$_4$ (TSTU), 1.2 eq., as a solid. The reaction is stirred for 30 minutes then concentrated by rotary evaporation followed by drying under high vac. A silica gel column is prepared with 2% water:acetonitrile as the mobile phase. The sample is loaded in 2% water:acetonitrile. The column is started with 2% water:acetonitrile and polarity is progressively increased to 5% water:acetonitrile and finally 80 mL 10% water:acetonitrile. The fractions containing product are identified by TLC in 10% water acetonitrile and confirmed by negative ion MS. This material has approximately 1 equivalent of DIEA by NMR.

Example 4

Sulfonation of Peptides

Model peptides and tryptic digests of various proteins were dissolved in about 20 μL of base which was prepared by mixing deionized water with diisopropylethylamine (DIEA) in the ratio of 19:1 v:v. Peptide mixtures from in-gel digests were concentrated to a final volume of about 20 μL and 1 μL of DIEA was added to make the solution basic. 5 μL of sulfonic acid active ester reagent at 100 mg/mL is added and the solution vortexed. The pH of each reaction is checked to ensure that it is still basic and adjusted if necessary. The reaction is allowed to proceed for 30 min. at RT. The samples are acidified with 5 μL of 1 N HCl and cleaned up directly using $C_{18}$ mini-columns ($\mu C_{18}$ Zip Tips™, Millipore, Bedford Mass.). The sulfonated peptides were eluted from the columns in 4–20 μL of acetonitrile: $H_2O$ (1:1 v:v) containing 0.1% TFA.

Example 5

Protection of Lys Side Chains by Guanidination and Subsequent Sulfonation of the Tryptic Peptides Model peptides and tryptic digests of various proteins were dissolved in about 20 μL of base which was prepared by mixing deionized water with diisopropylethylamine (DIEA) in the ratio of 19:1 v:v. Peptide mixtures from in-gel digests were concentrated to a final volume of about 20 μL and 1 μL of DIEA was added to make the solution basic. Two-μL of aqueous 0.5 M O-methylisourea hydrogensulfate was added and the solutions were vortexed. The pH of each solution was checked, and adjusted if necessary, to insure that they were still basic after addition of the guanidination reagent. The reactions were then allowed to proceed at room temperature (RT) for varying lengths of time (a few hours to two days). Typically, the room temperature reactions were allowed to proceed overnight. In the morning, 5 μL of sulfonic acid active ester reagent at 100 mg/mL is added and the solution vortexed. The pH of each reaction is checked to ensure that it is still basic and adjusted if necessary. The reaction is allowed to proceed for 30 min. at RT. The samples are acidified with 5 μL of 1 N HCl and cleaned up directly using $C_{18}$ mini-columns ($\mu C_{18}$ Zip Tips™, Millipore, Bedford Mass.). The guanidinated-sulfonated peptides were eluted from the columns in 4–20 μL of acetonitrile: $H_2O$ (1:1 v:v) containing 0.1% TFA.

Example 6

Experimental Description of the Instrument Used (FIG. 3)

Derivatized peptides were analyzed on an Applied Biosystems (Framingham, Mass. 01701) Voyager DE-STR time-of-flight mass spectrometer equipped with a $N_2$ laser (3 37 nm, 3 nsec pulse width, 20 Hz repetition rate). All mass spectra were acquired in the reflectron mode with delayed extraction. External mass calibration was performed with low-mass peptide standards, and mass measurement accuracy was typically ±0.2 Da. PSD fragment ion spectra were obtained after isolation of the appropriate derivatized precursor ions using timed ion selection. Fragment ions were refocused onto the final detector by stepping the voltage applied to the reflectron in the following ratios: 1.0000 (precursor ion segment), 0.9126, 0.6049, 0.4125, 0.2738, 0.1975 and 0.1273 (fragment ion segments). The individual segments were stitched together using software developed by Applied Biosystems. All precursor ion segments were acquired at low laser power (variable attenuator=1800) for <256 laser pulses to avoid detector saturation. The laser power was increased (variable attenuator=2100) for the remaining segments of the PSD acquisitions. The PSD data were acquired at a digitization rate of 20 MHz; therefore, all fragment ions were measured as chemically averaged and not monoisotopic masses. Mass calibration was done externally with peptide standards. Metastable ion decompositions were measured in all PSD experiments.

The PSD tandem mass spectra were searched in two ways against the NCBI non-redundant protein sequence database (most recent update at the time of the present filing was Mar. 2, 2001). First, uninterpreted PSD spectra were searched with the MS-Tag program from the Protein Prospector suite of search tools developed at UCSF (see P. R. Baker and K. R. Clauser, http://prospector.ucsf.edu). Search inputs included the measured precursor and fragment ion masses. The measured fragment ion masses of guanidinated peptides were decreased by 42 Da, the mass of the added guanidinium group, before searching against either database. The conservative error tolerances typically used were ±0.6 Da for the monoisotopic precursor ion and ±±2.0 Da for the chemically averaged fragment ions. Only y-type fragment ions were allowed possibilities. Other types of fragment ions like a, b, (b+$H_2O$), (b–$NH_3$) and internal cleavages were not considered because they are not prominent in the PSD spectra following sulfonation. Alternatively, the PSD data were manually interpreted. The derived sequence tags were searched using the MS-Edman program from the Protein Prospector software package. MS-Edman does not require the precursor or fragment ion masses as inputs. It only uses the measured sequence tags. The program considers all combinations of ambiguous residues, like (K, Q and E) or (I, L, N and D), which have similar masses.

Example 7

Database Description

The sequences of the polypeptide, and peptides thereof, may also be efficiently and accurately determined using software which accepts mass spectral fragmentation data, either uninterpreted y-ion series masses or sequence tags derived from the y-ion masses, as inputs for sequence database searches. Such search software commonly utilized by the skilled artisan include, but are not limited to, "Protein Prospector" (commercially available from the University of California at San Francisco or http://prospector.ucsf.edu) and "Peptide Search" (commercially available from the European Molecular Biology Laboratory at Heidelberg, Germany or http://www.mann.embl-heidelberg.de).

The fragmentation pattern produced by this invention can be searched against a number of sequence databases including, but not limited to, the NCBI non-redundant database (ncbi.nlm.nih.gov/blast/db.nr.z), SWISPROT (ncbi.nlm.gov/repository/SWISS-PROT/sprot33.dat.z), EMBL (FTP://ftp.ebi.ac.uk/pub/databases/peptidesearch/), OWL (ncbi.nlm.nih.gov/repository/owl/FASTA.z),dbEST (ncbi.nlm.nih.gov/repository/dbEST/dbEST.weekly.fasta.mmddyy.z) and Genebank (ncbi.nlm.nih.gov/genebank/genpept.fsa.z). The entire sequence of the polypeptide of interest can often be retrieved from the sequence database by searching the fragmentation data produced from one or more of the relevant peptide derivatives formed using the methods of this invention.

Of course, when using database searching techniques, it is most efficient to limit the searches by specifying that only y-ions or (y–NH3) ions are allowed fragments because y– and (y–NH3) ions are the most prominent species observed in the fragmentation patterns wherein the present methods are utilized. Other fragment ion types like a–, b–, (b+H2O), (b–H2O), (b–NH3) and internal cleavage ions can be disallowed because they are not prominent in the spectra of the peptides derivatized using the methods of the present invention. The derivatives formed with the present invention provide simple fragmentation patterns that often yield greater database search specificity than can be obtained from the spectra of the same peptides without derivatization.

Example 8 dPSD of NHS-ester Derivatized Proteins dPSD of NHS-ester Derivatized Tryptic Digest of a Model Protein: 4-vinyl-pyridine alcylated bovine serum albumin (4VP-BSA) (Sigma) was used as model protein for dPSD using NHS-esters.

Acylation with viniyl-pyridine: The lyophilised protein (2.4 mg) was dissolved in 800 µl of a buffer solution consisting of 8M urea, 50 mM Tris-HCl pH 8.0 and 50 mM DTT and incubated at 30° C. for 30 min. 10 µl 4-vinyl pyridine was added (to prevent formation of disulphide bonds) and the sample was incubated for another 1 h at 30° C. The sample was desalted using a NAP-10 column (Amersham Pharmacia Biotech), equilibrated with 100 mM $NH_4HCO_2$, pH8.8 and eluted in 1.2 ml.

The sample was digested with trypsin (Promega), 1 µg trypsin/100 µg protein, for 6 h at 30° C. and the reaction was stopped by the addition of TFA to a final concentration of 1%. The digest was diluted in 50% AcN:0.5% TFA to a final concentration of 100 ng/µl (1.5 pmol/µl).

N-terminal derivatization with NHS-ester of 3-Sulfopropionic acid anhydride: Tryptic digest of 4VP-BSA (3 pmole) were dried on a speed vac and reconstituted in 10 µl of deionized $H_2O$:diisopropylethylamine (19:1, v:v). The NHS-ester was dissolved in deionized $H_2O$ (10 mg NHS-ester/100 µl $H_2O$) and 5 µl were added to each sample. The reaction mixture was vortexed and left for 15 minutes at room temperature to react. The samples were acidified by adding 1 µl 10% TFA and purified through $\mu C_{18}$ ziptips (Millipore) according the instructions of the manufacturer. The sample was eluted directly on the MALDI-target with a saturated solution of alpha-cyano-4-hydroxycinnamic acid in 50% AcN:0.1% TFA and analyzed in reflectron positive mode and PSD mode positive mode using the Ettan™ MALDI-ToF.

dPSD of NHS-ester Derivatized Tryptic Digests of Proteins from E-coli

Preparation of low speed supernatant of *Escherichia coli*- *Escherichia coli* (*E-coli*), (40 µg stain B, ATCC 11303) was put in 20 ml reducing buffer containing 8M urea/4% chaps, 2% 3–10 pharmalyt, 65 mM DTT. The cells were disrupted by sonication (7×20s with cooling on ice in between). The lysate was centrifuged at 10.000×g for 40 min at 8° C. The low speed supernatant (LSS) was stored in −20° C. until used.

Separation by 2-dimensional (2D) electrophoresis-LSS of *E-coli* (1 mg) was diluted in IPG rehydration buffer (8M urea/2% CHAPS/ 2% IPG buffer 4–7/ 10 mM DTT) and rehydrated into the IPG strips (24 cm, pH 3–10 NL, Amersham Pharmacia Biotech) overnight. 2D-electophoresis was performed following the instructions of the manufacture. After separation by 2D-electrophoresis, the gels were fixed in 40% ethanol (EtOH), 10% acetic acid (HAc) for 1 h, stained with, 0.1% Commassie brilliant blue in 40% EtOH, 10% HAc, for 30 min and destained in 20% EtOH, 5 % HAc overnight.

Trypsin digestion: Spots of proteins (1.4mm in diameter) of medium (~low pmole) to low intensity (~high fmole) were picked and transferred to a microtiter plate using the Ettan™ spot picker (Amersham Pharmacia Biotech). The proteins were destained with 100 ul, 50% methanol, 50 mM ammoniumbicarbonat (AMBIC), 3×30minutes, dried in a Tubo-Vap for 15 minutes and digested with 5 ul trypsin for 60 minutes at 37° C. (40ng/ ul 20 mM AMBIC, Promega) using the Ettan™ TA Digester (Amersham Pharmacia Biotech). The peptides were extracted using 35 ul 50% acetonitrile, 0.5% TFA 2×20 minutes. The extracts were dried at room temperature overnight.

N-terminal derivatization: The samples were reconstituted in 20 µl deionized $H_2O$. One µl (20%) of each sample was mixed 1:1 with alpha cyano matrix solution and analysed in reflectrone positive mode using the Ettan™ MALDI-ToF. To the remaining 19 µl of each sample, 1 µl DIEA and 5 µl sulfopropionic NHS-ester solution, 10 mg/100 µl were added. The samples were thoroughly mixed by pipeting and left to react for 15 minutes at room temperature. TFA (1 µl, 10%) was added to each sample and purified through $\mu C_{18}$ ziptips (Millipore). The samples were eluted directly on the MALDI-target with a saturated solution of alpha-cyano-4-hydroxycinnamic acid in 50% AcN:0.1% TFA and analyzed in reflector positive mode and PSD positive mode using the Ettan™ MALDI-ToF.

Automated dPSD Using NHS-esters

The current chemistry is well suited for automation. Using Ettan™ digester and Ettan™ spotter the sample handling and reaction mixtures can be automatically processed. Experimentally, the model peptides or peptide mixtures placed in individual wells of a microtiterplate are reconstituted in 100 ul water (quality of 18 MΩ or better). At this point the liquid handle can split the sample into two reactions. One, containing 5 ul, for direct analysis in the MS, and the other for chemical modification. The material designated for chemical modification is dried at room temperature for one hour. The handler (e.g. a Gilson 215 multiprobe) then reconstitutes the dried material by addition of 10 ul of the reactive derivatisation reagent in a buffer containing DIEA (Diisopropylethylamine). The reactants are mixed by repeated aspiration. The chemical modification step is allowed to proceed for approximately 15 minutes at room temperature. The samples are finally worked up in the same fashion as previously described, and analysed in the MS.

Results

Quantitative N-terminal derivatization of tryptic peptides of 4VP-BSA was obtained with NHS-ester of 3-sulfopropionic acid anhydride in aqueous solution. FIG. 4 and 5 show the reflectron spectra of non-derivatized and derivatized 4VP-BSA respectively. The peptides I–III were used for dPSD analyses, (FIG. 6–8). The fragmentation spectra showed exclusively y-ions. The fragmentation data from each of the three peptides could be used for unambiguous identification against the NCBInr protein sequence database (PepFrag,www.proteometric.com).

Two gel plugs, containing proteins of *E-coli* from a commassie stained 2D-gel were identified with dPSD using NHS-ester. The proteins were digested with trypsin, extracted from the gel plug and derivatized as described. FIG. 9 and 10 show the reflectrone spectra of non-derivatized and derivatized sample from one of the gel plugs. The peptide marked with a circle was quantitatively derivatized and used for PSD analysis (FIG. 11). The masses of the fragment ions (y-ions) were used for protein identification in PepFrag. The suggested candidate from PepFrag agreed with the candidate obtained by searching the tryptic map in ProFound (proteometrics.com). Reflectron spectra of non-derivatized and NHS-ester derivatized sample from the second gel plug are shown in FIG. 12 and 13. The peptide, m/z 1569 was quantitatively derivatized (m/z 1705) and used for PSD analyses (FIG. 14). The y-ions obtained were used for protein identification in PepFrag, showing the same candidate as obtained with peptide masses in ProFound.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method of identifying a polypeptide, which method comprises the steps of
    (a) derivatizating, in an aqueous solution, the N-terminus of the polypeptide, or the N-termini of one or more peptides of the polypeptide, with at least one acidic reagent containing a sulfo moiety coupled to an ester moiety to provide one or more peptide derivatives, which reagent exhibits a half-life in aqueous solution of not less than 10 minutes at room temperature, to prepare one or more derivatives;
    (b) analyzing at least one said derivative using a mass spectrometric technique to provide a fragmentation pattern; and
    (c) interpreting the fragmentation pattern obtained to identify the polypeptide;

wherein said at least one acidic reagent is an N-hydroxysuccinimide ester of the compound of the formula

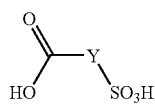

wherein Y is a spacer which contains aliphatic and/or aromatic fragments and may optionally include additional sulfonic acids.

2. The method according to claim 1, wherein the acidic reagent has a pKa of less than about 2 when coupled to the polypeptide.

3. The method according to claim 1, wherein the mass spectrometric technique used in step (b) is matrix-assisted laser desorption ionization (MALDI) mass spectrometry.

4. The method according to claim 1, wherein the mass spectrometric technique used in step (b) is electrospray ionization (ESI).

5. The method according to claim 1, wherein in step (c), the fragmentation pattern is interpreted using a software program or database.

6. The method according to claim 1, wherein all the steps are conducted as part of an automated or semi-automated procedure.

7. The method according to claim 1, wherein the acidic reagent comprises a 3-sulfopropionic acid N-hydroxysuccinimide ester.

8. The method according to claim 1, wherein the acidic reagent comprises a 2-sulfobenzoic acid N-hydroxysuccinimide ester.

9. The method according to claim 1, wherein the polypeptide has been obtained by enzymatic digestion.

10. The method according to claim 9, wherein the enzyme is trypsin.

11. The method according to claim 1, which further comprises a step of protecting lysine residues prior to the derivatizating step.

* * * * *